US007507226B2

(12) United States Patent  (10) Patent No.: US 7,507,226 B2
Stanus et al.                (45) Date of Patent:    Mar. 24, 2009

(54) ACCESS PORT WITH SAFETY TAB AND FLUID CONTAINER EMPLOYING SAME

(75) Inventors: Johanny B. P. Stanus, Gibecq (BE); Eric J. Hénaut, Arquennes (BE)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 272 days.

(21) Appl. No.: 11/139,244

(22) Filed: May 27, 2005

(65) Prior Publication Data

US 2005/0283132 A1    Dec. 22, 2005

Related U.S. Application Data

(63) Continuation-in-part of application No. 10/277,432, filed on Oct. 22, 2002.

(51) Int. Cl.
*A61M 1/36* (2006.01)
(52) U.S. Cl. .................. 604/414; 604/411; 604/415
(58) Field of Classification Search ............... 604/6.16, 604/264, 403, 408, 411, 414, 533, 200, 201, 604/204, 167.01, 167.03, 167.05, 27, 33, 604/905, 220; 383/210.1; 222/83, 96, 104, 222/153.05–7, 548
See application file for complete search history.

(56) References Cited

U.S. PATENT DOCUMENTS

| | | | |
|---|---|---|---|
| 1,259,057 A | 3/1918 | Vick | |
| 2,073,292 A | 3/1937 | Waite et al. | |
| 2,849,256 A | 8/1958 | Kowal | |
| 3,512,524 A | 5/1970 | Drewe | |
| 3,653,546 A | 4/1972 | Hazard | |
| 3,844,283 A | 10/1974 | Dabney | |
| 3,986,508 A | 10/1976 | Barrington | |

(Continued)

FOREIGN PATENT DOCUMENTS

CA    1333704 A1    12/1994

(Continued)

OTHER PUBLICATIONS

International Search Report for International Applicaton No. PCT/US2006/019728 dated Oct. 26, 2006.

(Continued)

*Primary Examiner*—Leslie R Deak
(74) *Attorney, Agent, or Firm*—Ira D. Finkelstein; Bell, Boyd & Lloyd LLP

(57) ABSTRACT

An access port for a medical fluid container is provided and in one embodiment includes: (i) a shell; (ii) a perforator located within the shell, the perforator including an end configured to pierce a medical fluid container; and (iii) a safety tab connected to the perforator, the safety tab initially preventing the perforator from piercing the medical fluid container, the safety tab manually removable to enable the perforator to pierce the medical fluid container. The shell can include a pair of hingedly moving arms and members connected hingedly to the arms, the members operable to push the perforator towards the medical fluid container when the arms are pushed. The safety tab can include a plurality of frangible fixtures, the fixtures collectively providing a suitably high tamper resistance force, the fixtures individually providing a suitably low tab removal force.

8 Claims, 23 Drawing Sheets

U.S. PATENT DOCUMENTS

| | | | |
|---|---|---|---|
| 4,062,466 A * | 12/1977 | Conti | 215/252 |
| RE29,656 E | 6/1978 | Chittenden et al. | |
| 4,200,100 A | 4/1980 | Willis | |
| 4,201,208 A | 5/1980 | Cambio, Jr. | |
| 4,314,654 A | 2/1982 | Gaubert | |
| 4,322,018 A | 3/1982 | Rutter | |
| 4,364,387 A | 12/1982 | Larkin | |
| 4,405,163 A | 9/1983 | Voges et al. | |
| 4,416,395 A | 11/1983 | Gaubert | |
| 4,475,566 A | 10/1984 | Haines | |
| 4,548,606 A | 10/1985 | Larkin | |
| 4,567,999 A | 2/1986 | Hjertman et al. | |
| 4,576,211 A | 3/1986 | Valentini et al. | |
| 4,632,673 A | 12/1986 | Tiitola et al. | |
| 4,676,775 A | 6/1987 | Zolnierczyk et al. | |
| 4,681,243 A | 7/1987 | Takasugi | |
| 4,696,411 A | 9/1987 | Graf et al. | |
| 4,735,608 A | 4/1988 | Sardam | |
| 4,785,858 A | 11/1988 | Valentini et al. | |
| 4,787,429 A | 11/1988 | Valentini et al. | |
| 4,798,605 A | 1/1989 | Steiner et al. | |
| 4,838,858 A | 6/1989 | Wortham et al. | |
| 4,872,494 A | 10/1989 | Coccia | |
| 4,909,290 A | 3/1990 | Coccia | |
| 4,927,423 A | 5/1990 | Malmborg | |
| 4,961,728 A | 10/1990 | Kosinski | |
| 4,973,310 A | 11/1990 | Kosinski | |
| 5,135,507 A | 8/1992 | Haber et al. | |
| 5,188,597 A | 2/1993 | Sweeney et al. | |
| 5,279,583 A | 1/1994 | Shober, Jr. et al. | |
| 5,304,192 A | 4/1994 | Crouse | |
| 5,308,347 A | 5/1994 | Sunago et al. | |
| 5,334,180 A * | 8/1994 | Adolf et al. | 604/411 |
| 5,337,775 A | 8/1994 | Lane et al. | |
| 5,352,191 A * | 10/1994 | Sunago et al. | 604/7 |
| 5,389,085 A | 2/1995 | D'Alessio et al. | |
| 5,425,367 A | 6/1995 | Shapiro et al. | |
| 5,445,630 A | 8/1995 | Richmond | |
| 5,456,678 A | 10/1995 | Nicoletti | |
| 5,480,385 A | 1/1996 | Thorne et al. | |
| 5,514,123 A | 5/1996 | Adolf et al. | |
| 5,542,927 A | 8/1996 | Thorne et al. | |
| 5,549,708 A | 8/1996 | Thorne et al. | |
| 5,603,706 A | 2/1997 | Wyatt et al. | |
| 5,616,129 A | 4/1997 | Mayer | |
| 5,616,130 A | 4/1997 | Mayer | |
| 5,685,863 A | 11/1997 | Botich et al. | |
| 5,709,667 A | 1/1998 | Carilli | |
| 5,746,727 A | 5/1998 | Graves et al. | |
| 5,766,147 A | 6/1998 | Sancoff et al. | |
| 5,769,138 A | 6/1998 | Sadowski et al. | |
| 5,795,336 A | 8/1998 | Romano et al. | |
| 5,810,398 A | 9/1998 | Matkovich | |
| 5,817,082 A | 10/1998 | Niedospial, Jr. et al. | |
| 5,868,433 A | 2/1999 | Matkovich | |
| 5,868,713 A | 2/1999 | Klippenstein | |
| 5,873,872 A | 2/1999 | Thibault et al. | |
| 5,895,383 A | 4/1999 | Niedospial, Jr. | |
| 5,960,992 A | 10/1999 | Bernstein et al. | |
| 5,975,163 A | 11/1999 | Gianfranco | |
| 5,976,115 A | 11/1999 | Parris et al. | |
| 6,050,978 A | 4/2000 | Orr et al. | |
| 6,070,623 A | 6/2000 | Aneas | |
| 6,071,366 A | 6/2000 | Yamada | |
| 6,082,584 A | 7/2000 | Stern | |
| 6,142,446 A | 11/2000 | Leinsing | |
| 6,161,728 A | 12/2000 | Dark | |
| 6,186,979 B1 | 2/2001 | Dysarz | |
| 6,220,482 B1 | 4/2001 | Simmel et al. | |
| 6,223,924 B1 | 5/2001 | Ek et al. | |
| 6,253,804 B1 | 7/2001 | Safabash | |
| 6,258,078 B1 | 7/2001 | Thilly | |
| 6,279,779 B1 | 8/2001 | Laciacera et al. | |
| 6,280,431 B1 | 8/2001 | Domkowski et al. | |
| 6,293,431 B1 | 9/2001 | Seymour et al. | |
| 6,341,802 B1 | 1/2002 | Matkovich | |
| 6,378,714 B1 | 4/2002 | Jansen et al. | |
| 6,478,771 B1 | 11/2002 | Lavi et al. | |
| 6,478,788 B1 | 11/2002 | Aneas | |
| 6,536,805 B2 | 3/2003 | Matkovich | |
| 6,537,263 B1 | 3/2003 | Aneas | |
| 6,540,732 B1 | 4/2003 | Botich et al. | |
| 6,601,721 B2 | 8/2003 | Jansen et al. | |
| 6,626,309 B1 | 9/2003 | Jansen et al. | |
| 6,645,181 B1 * | 11/2003 | Lavi et al. | 604/191 |
| 6,655,655 B1 | 12/2003 | Matkovich et al. | |
| 6,689,092 B2 | 2/2004 | Zierenberg et al. | |
| 6,709,424 B1 | 3/2004 | Knierbein | |
| 6,726,672 B1 | 4/2004 | Hanly et al. | |
| 6,786,875 B2 | 9/2004 | Barker et al. | |
| 2001/0003996 A1 | 6/2001 | Jansen et al. | |
| 2002/0045843 A1 | 4/2002 | Barker et al. | |
| 2002/0058908 A1 | 5/2002 | Zierenberg et al. | |
| 2002/0093192 A1 | 7/2002 | Matkovich | |
| 2002/0121496 A1 | 9/2002 | Thiebault et al. | |
| 2002/0128628 A1 * | 9/2002 | Fathallah | 604/411 |
| 2002/0128629 A1 | 9/2002 | Antoine | |
| 2002/0193777 A1 | 12/2002 | Aneas | |
| 2004/0015126 A1 | 1/2004 | Zierenberg | |
| 2004/0015134 A1 | 1/2004 | Lavi et al. | |
| 2004/0078025 A1 | 4/2004 | Botich et al. | |

FOREIGN PATENT DOCUMENTS

| | | |
|---|---|---|
| EP | 0 280 528 A2 | 8/1988 |
| EP | 0 376 697 A2 | 7/1990 |
| EP | 0 376 698 A2 | 7/1990 |
| EP | 0 381 697 B1 | 8/1990 |
| EP | 0416454 | 3/1991 |
| EP | 0 566 305 A3 | 10/1993 |
| EP | 0 568 525 B1 | 11/1993 |
| EP | 0 829 251 A3 | 3/1998 |
| EP | 0 954 249 B1 | 10/1999 |
| EP | 0 962 230 A3 | 12/1999 |
| EP | 0 988 871 B1 | 3/2000 |
| EP | 1 011 765 B1 | 6/2000 |
| EP | 1 029 526 | 8/2000 |
| EP | 1060730 | 12/2000 |
| EP | 1081054 | 7/2001 |
| LU | 90268 | 4/2000 |
| WO | WO 86/06966 | 12/1986 |
| WO | WO 93/20772 | 10/1993 |
| WO | WO93/20772 | 10/1993 |
| WO | WO 95/05863 | 3/1995 |
| WO | WO 97/36783 | 10/1997 |
| WO | WO 98/17192 | 4/1998 |
| WO | WO 98/44971 | 10/1998 |
| WO | WO 99/23947 | 5/1999 |
| WO | WO 00/24357 | 5/2000 |
| WO | WO 00/29049 | 5/2000 |
| WO | WO 00/35367 | 6/2000 |
| WO | WO 01/28490 A1 | 4/2001 |
| WO | WO 01/60276 A1 | 8/2001 |
| WO | WO 02/32372 A1 | 4/2002 |
| WO | WO 03/100424 A3 | 12/2003 |
| WO | WO2004/037337 | 5/2004 |
| WO | WO 2004/060445 A2 | 7/2004 |

OTHER PUBLICATIONS

International Search Report (7 pgs.).
European Search Report of EP 07015108.8 dated Sep. 20, 2007.

* cited by examiner

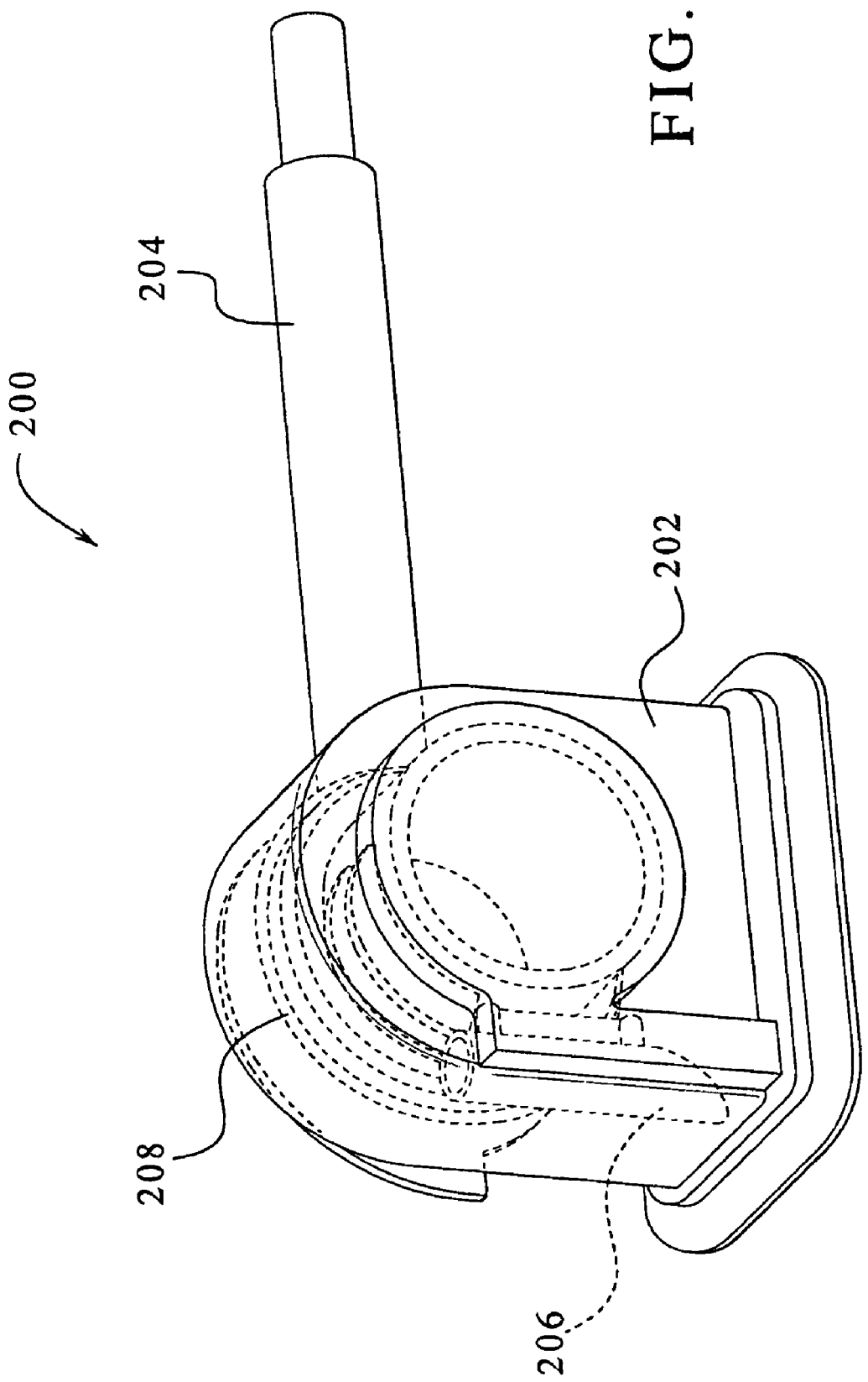

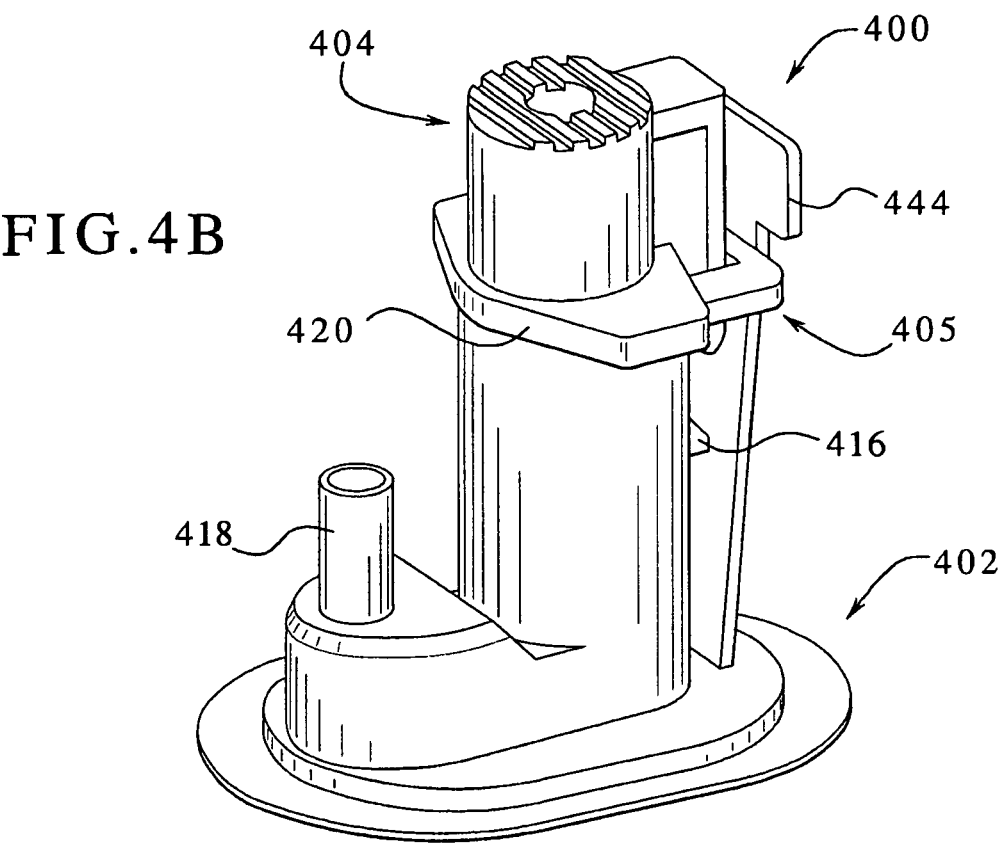
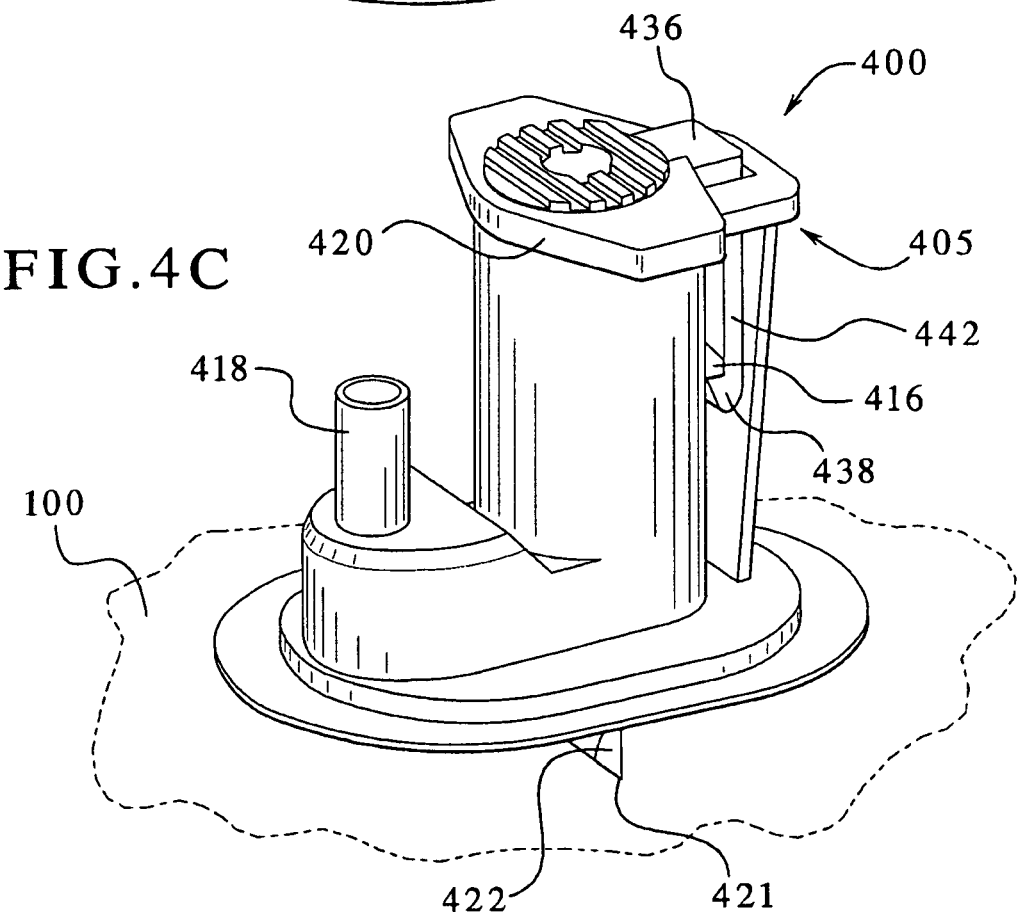

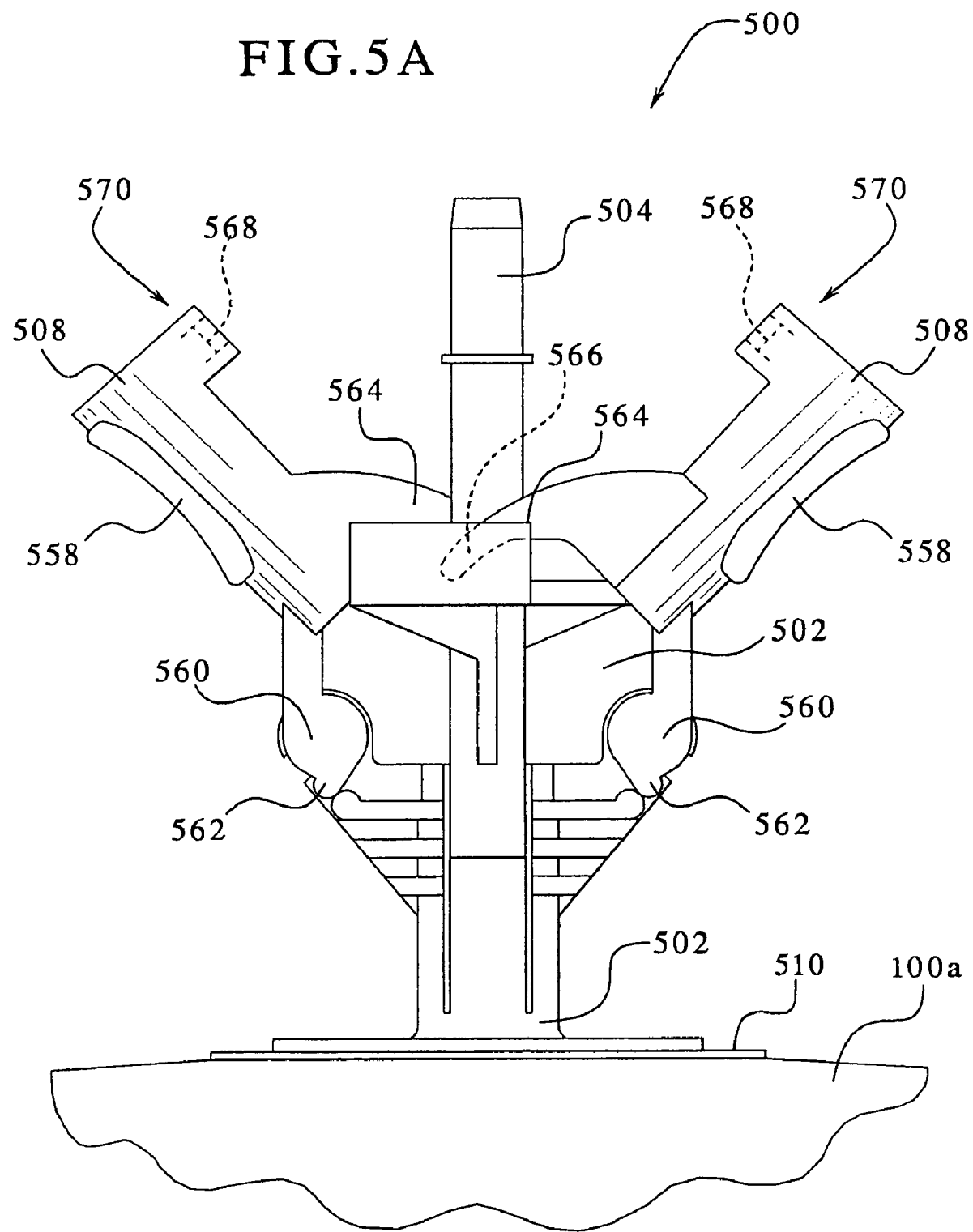

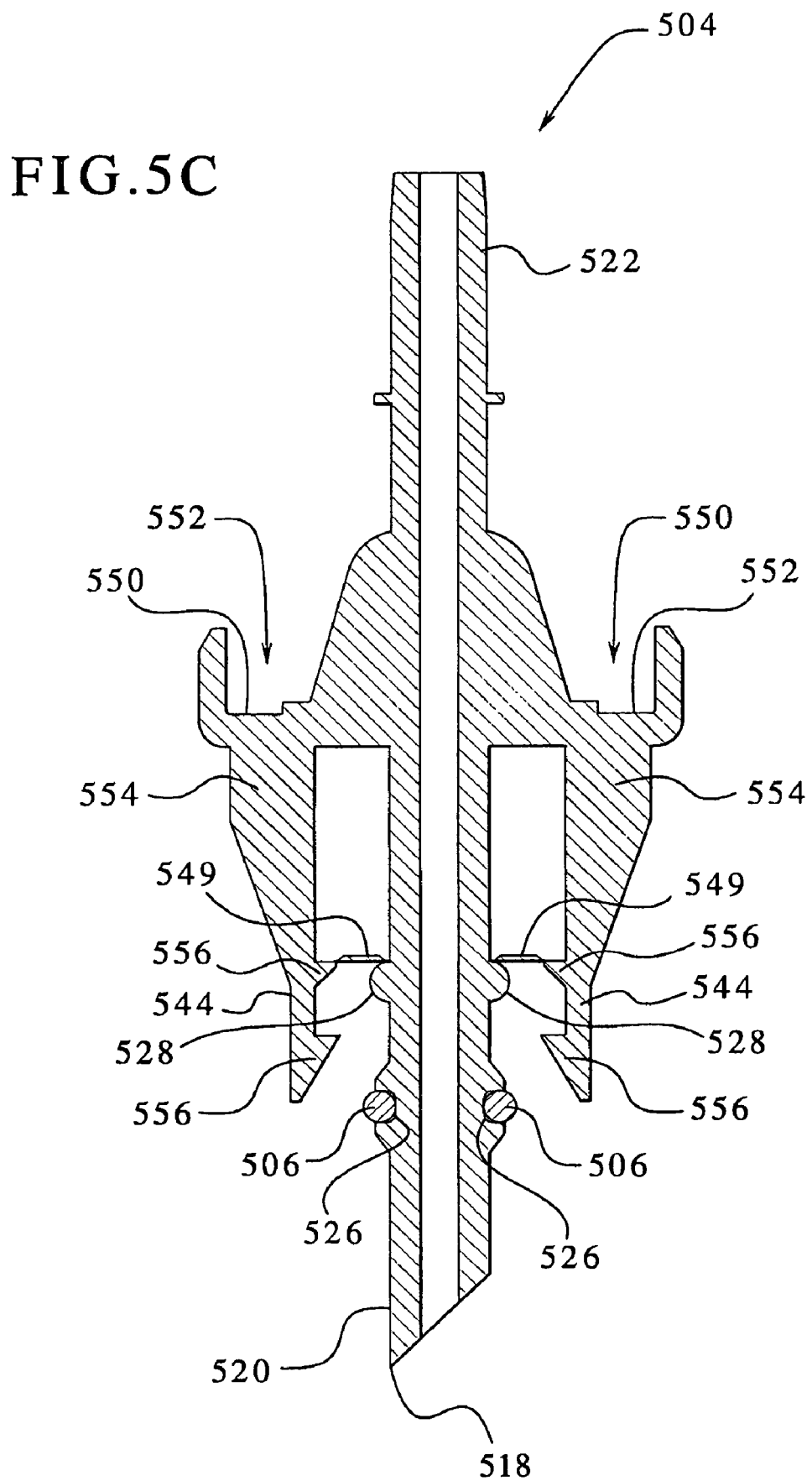

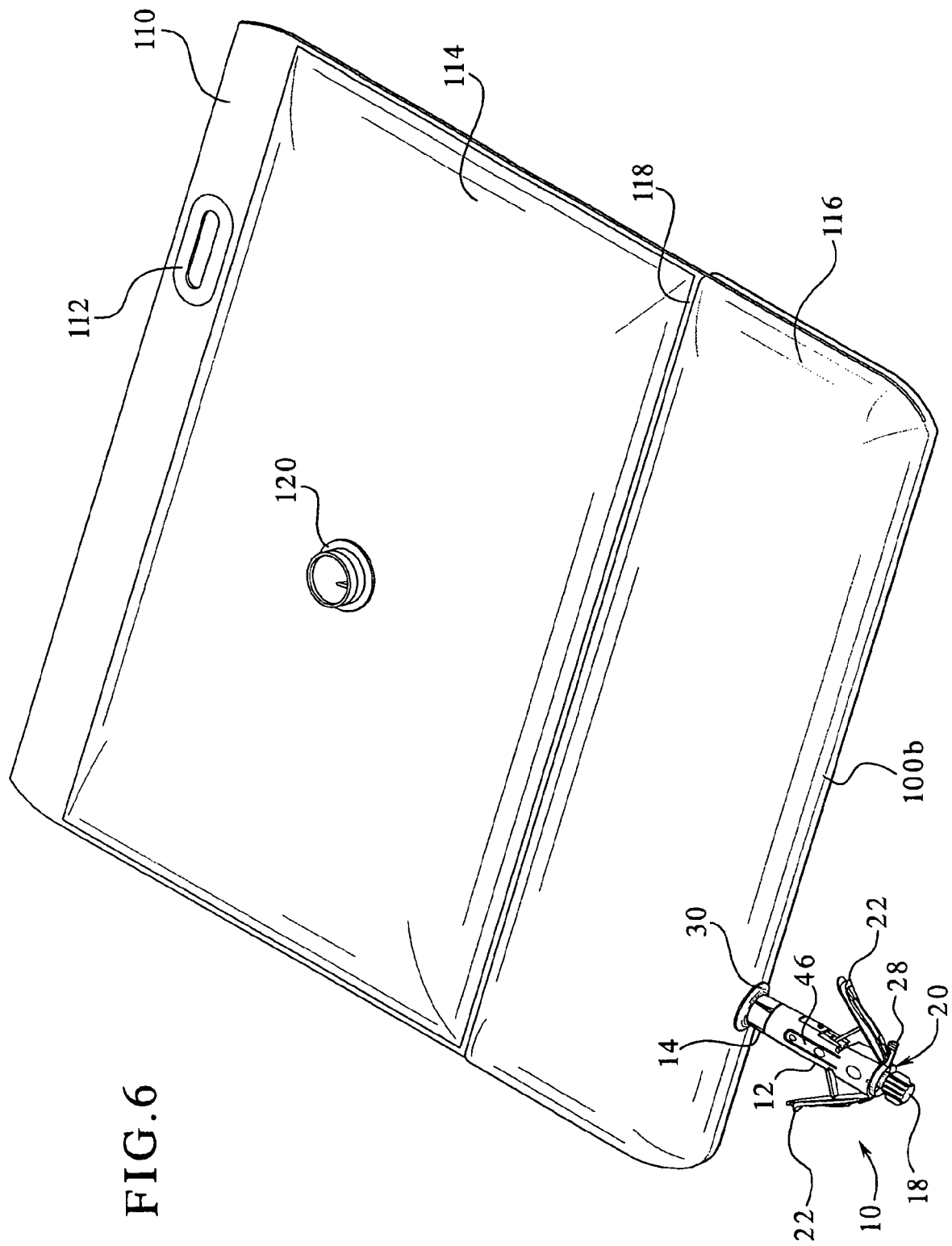

ACCESS PORT WITH SAFETY TAB AND FLUID CONTAINER EMPLOYING SAME

PRIORITY CLAIM

This patent claims priority to and the benefit as a continuation-in-part of U.S. patent application Ser. No. 10/277,432, filed Oct. 22, 2002, titled "Formed, Filled, Sealed Solution Container, Port And Method For Establishing Flow Between The Container And An Administration Set."

BACKGROUND OF THE INVENTION

The present invention generally relates to a container, an access port and a method for establishing flow between the container and an administration set. The access port may establish flow of fluid from the container into an appropriate administration set. More specifically, a valve or base that seals to a container is provided. A perforator or plunger in the valve punctures the container and provides access to the solution in the container.

Containers for the administration of medical solutions are well known. Typically, the containers are made from flexible film that is folded and sealed together along peripheral side edges. Further, the containers typically have an inlet and an outlet. The containers further typically have a device for piercing the outlet and establishing a fluid communication between the device and the solution inside the container. The solution may then be exhausted from the device to an administration set and/or patient.

Maintaining the sterility of the medical solution to be administered to the patient is extremely important. However, handling of the medical solution container may create risks of contamination. The risk of contamination may increase in emergency situations where quick manipulation on the various components may introduce bacteria or other pathogens into the container. For example, a user may inadvertently touch and/or contaminate a sterile end surface of an inlet or an outlet. The contamination may then be transferred to the contents of the container.

Further, containers for the administration of medical solutions are typically flexible. Accordingly, making a sterile connection to the flexible container for withdrawing the contents in a sterile manner may be difficult. For example, U.S. Reissue Pat. No. Re. 29,656 to Chittenden et al. discloses an additive transfer unit having a tubular member that seals to a solution container. The unit includes a needle that punctures a stopper of the solution container. Obtaining a liquid-tight and leakproof connection through the flexible container using traditional medical connectors such as, for example, needles or piercing pins is difficult.

Further, administration ports are securely bonded to the flexible container. However, the administration ports of known flexible solution containers are often the weakest part of the container. Accordingly, certain medical solutions which are sensitive to oxygen and/or other penetrating gases may be compromised. Further, pre-formed administration ports constitute potential sites of leakage and are potential points of contaminant ingress.

Other means for establishing a fluid connection between the container and an administration set are also known. Generally, known access ports require a two-handed operated access port and do not produce audible or visible notification when the access port is fully engaged. Further, many of the known access ports do not substantially protect against touch and air-borne contaminants.

A need, therefore, exists for a formed, filled, sealed solution container with an access port and a method for establishing flow between the container and an administration set. Accordingly, a medical solution container having an improved inlet and outlet port to reduce the likelihood of contamination during storage and/or use is needed. Further, a medical solution container and access port with improved ease of handling is needed. Further still, a solution container and an access port with a liquid tight seal to avoid leaking, minimize touch and/or airborne contamination and minimize permeation of oxygen and/or other gases are needed.

SUMMARY OF THE INVENTION

The present invention provides a formed, filled, sealed solution container with an access port and a method for establishing a fluid connection between the container and an administration set. More specifically, the port is sealed to the container and has means to puncture said container. The fluid in the container is removed from the container through the port to an administration line. The administration line further carries the fluid to an administration set.

The port may have a valve and a perforator. The valve may include a peripheral sealing flange or ring that may allow for sealing to the container. The valve may define a cylindrical opening that may receive and slidingly couple to a perforator or plunger. The cylindrical opening may guide the perforator or plunger to puncture the container and open access to the solution contained therein. The perforator or plunger may have a hollow shaft that includes a tri-slope bevel on the end facing the film of the container. The tri-slope bevel of the perforator or plunger punctures and tears a stretched film of the container below the sealing flange of the valve.

The present invention may provide single-handed operation and may provide audible and visible notification when the tri-slope bevel has punctured the film to allow solution flow. Further, the present invention may fully shroud the fluid generation path to exclude touch and air-borne contamination. The present invention may further reduce the amount of force needed to penetrate the film of the container. Further, the perforator or plunger of the present invention may not be removed from the fluid engagement position, after engagement is achieved.

In one embodiment an access port that enables access to containers holding a solution, such as a plastic bag that holds a sterile medical fluid is provided. The container can be constructed in a form, fill and seal operation and can be constructed for example from a Clearflex™ material. The containers can include, for example, peritoneal dialysis solution or other solution used in a continuous renal replacement therapy ("CRRT"). The access port establishes the flow of fluid from the containers into a corresponding administration set or the like.

The access port includes: (i) a perforation assembly and (ii) a valve. The valve is sealed to the container. The valve can include a peripheral sealing flange or ring that allows it to be, e.g., sonically, sealed to the container film. The valve receives and slidingly couples to the perforation assembly. The perforation assembly includes a perforator and a shell. The perforator moves within the shell of the perforation assembly to puncture the container and open access to the solution contained therein.

The perforator, in one preferred embodiment, is a hollow shaft that includes a sloped bevel on the end facing the container. The sloped bevel of the perforator punctures and tears the wall of the container contained within the valve.

The access port allows for one-handed operation and provides audible and visible notification when the sloped bevel has punctured the container to allow solution flow. The access port shrouds the fluid generation path fully to exclude touch and air-borne contamination. The access port reduces the amount of force needed to penetrate the container and precludes removal of the perforator from a fluid engagement position once engagement is achieved.

The access port operates with a medical fluid container, which contains a valve sealed to a wall of the container. The access port includes a shell. The shell fastens onto the valve of the container. In particular, the shell includes a bottom portion that snap-fits over the valve sealed to the solution container.

The shell 12 encloses a perforator. The perforator extends out of the top of the shell and includes a threaded end, which is protected initially by a threaded cap. The perforator also includes a removable safety or tamper proof tab. When the tab is connected to the perforator, the operator is precluded from pressing rotatable arms of the shell inward, which action pushes the perforator downward with respect to the shell of the access port. The operator can connect a device such as an administration set with luer connector to the perforator in a fluid-tight manner by removing the cap and connecting the device via threads located at the top of the perforator. With the access port installed in the valve and the safety tab removed, the arms can be then pressed inwardly to cause the perforator to move and puncture the valve of the solution container.

The safety tab includes a ring that extends around a circular flange, which projects radially outwardly from a hollow shaft of the perforator. The ring is connected to the flange at a multitude of, e.g., eight, frangible points. The ring of the safety tab is connected also to a handle. The operator grasps the handle and tears the ring from the circular flange by rupturing the eight points or fixtures. The diameter of the flange is smaller than the inner diameter of the hollow shell, so that the flange and associated perforator shaft can move within the shell after the ring and the handle are removed from the flange.

To the above-described ends, in one embodiment a container is provided. The container has a film, a port and a tab. The film is folded to define sides and the sides are sealed to define an interior. The port defines an outlet through which fluid communication with the interior is established. The tab is attached to the port and the tab identifies establishment of fluid communication with the interior.

In this first embodiment, the tab of the container can be detached from the port after fluid communication is established. The container can have a perforator attached to the port, wherein the tab is attached to the perforator and attached to the port, and further wherein the tab is detached from the perforator after the fluid communication is established. The container can further have a shell having a first part attached to a second part defining the tab, wherein detachment of the first part from the second part identifies establishment of the fluid communication. The container still further can have a cock attached to the port wherein the tab is attached to the cock, and further wherein the tab is removed from the cock before the fluid communication is established. Identification of the establishment of fluid communication by the tab can produce an audible notification. Moreover, the container can further have a line having a first end and a second end wherein the first end is attached to the port.

In a second embodiment, a port for establishing fluid flow from a container to an administration set is provided. The port has a valve with a housing defining an interior, a shoulder on the housing, a cock, a catch, and a plunger. The cock is attachable to the valve and axially guided by the shoulder of the housing. The catch on the valve locks the cock and locking of the cock produces a sound. The plunger has a hollow shaft and a tip. The plunger is in the interior of the valve and rotation of the cock forces the plunger to protrude from the interior of the valve and forces the tip to penetrate the container. The tip of the plunger is locked in the container after the cock is locked.

In this second embodiment, the port can have a gasket on the plunger and/or a removable tab on the cock, wherein the tab impedes rotation of the cock. The port can further have a knob associated with the plunger, wherein the knob guides the plunger in the valve, and further wherein the knob prevents rotation of the plunger. The port can further have a peripheral foot section integrally formed with the valve wherein the peripheral foot section is sealed to the container.

In a third embodiment, a method for establishing flow between a container and an administration set is provided. The method includes: (i) providing a port having a valve, cock and plunger wherein the valve has an interior for housing the cock and the plunger; (ii) attaching the port to the container; (iii) sealing the valve of the port to the container; (iv) rotating the cock so that the cock applies a force on the plunger; (v) piercing the container with the plunger; (vi) locking the cock and the plunger in a position; and (vii) producing an audible notification upon locking the cock and the plunger in the position.

In this third embodiment, the method can further include: (viii) providing a gasket wherein a seal between the plunger and the valve is maintained with the gasket; (ix) providing a tab on the cock; (x) removing the tab from the cock; (xi) providing a line attachable to the cock; (xii) embedding the plunger into the container; and/or (xiii) locking the cock into the valve.

In a fourth embodiment, a port for establishing fluid flow from a container to an administration set is provided. The port has a valve having a shafts a perforator having an arm wherein the perforator is axially guided by the shaft of the valve, a cantilever beam protruding from the valve and a shell. The cantilever beam prevents the perforator from exiting the valve. The shell has a first part attached to a second part. The shell engages the valve and forces the perforator to pierce the container and the first part of the shell detaches from the second part of the shell after the perforator pierces the container.

In this fourth embodiment, the port can further include: (i) a gasket on the perforator, wherein the gasket provides a seal between the perforator and the valve; (ii) a finger pad on the first part of the shell; (iii) slots on the valve to receive the arm of the perforator; (iv) a flange on the perforator to guide the perforator in the shaft of the valve; (v) a protrusion on the valve wherein the protrusion mates with the shell; and/or (vi) a wing on the shell wherein the shell is manipulated by applying force to the wing.

In a fifth embodiment, a method for establishing flow between a container with a port and an administration set is provided. The method includes: (i) providing a valve, a perforator and a shell, wherein the valve has an interior and the perforator is in the interior of the valve, and further wherein the perforator protrudes from the valve; (ii) sealing the valve to the container; (iii) attaching the shell to the valve; (iv) forcing the perforator to pierce the container by rotation of the shell; (v) piercing the bag with the perforator; (vi) locking the perforator in a position; and (vii) maintaining a seal between the perforator and the valve.

In this fifth embodiment the method can further include: (viii) rotating the shell, wherein rotation of the shell produces an axial stroke of the perforator; (ix) embedding the perforator into the container; and/or (x) locking the perforator into the valve.

In a sixth embodiment, a port for establishing fluid flow from a container is provided. The port has a valve having a shaft, a perforator in the shaft of the valve, a beam on the perforator, and a latch on the valve. The valve seals to the container. The beam has a catch and the latch on the valve mates with the catch of the beam. The mating of the latch and the catch locks the perforator.

In this sixth embodiment, the mating of the latch and the catch can produce a sound and the perforator can be hollow. Also, the port can further include a line attached to the shaft of the valve and/or an arm on the beam for locking the perforator in the valve.

In a seventh embodiment, a method for establishing fluid flow between a container and an administration set is provided. The method includes: (i) providing a port having a gasket, a valve and a perforator, wherein the valve has an interior, and further wherein the perforator is in the interior of the valve; (ii) sealing the valve of the port to the container; (iii) applying pressure to the perforator and forcing the perforator to pierce the container; (iv) locking the perforator and the valve in an activated position; and (v) maintaining a seal between the perforator and the valve with the gasket.

This method can further include: (vi) breaking the seal between the valve and the container; (vii) attaching a line to the valve; and/or (viii) locking the perforator in the valve so that rotation of the perforator is prevented.

In an eighth embodiment, a port for establishing fluid flow from a container to an administration set is provided. The port has a valve defining a shaft, a perforator in the shaft of the valve, a first wing and a second wing, a latch on the first wing and a catch on the second wing. The valve is sealed to the container and the latch locks to the catch. The first wing and the second wing are diametrically opposed and attached to the valve. Further, the first wing and the second wing contact the perforator wherein rotation of the first wing and the second wing forces the perforator to move toward the container.

In this eighth embodiment, locking of the latch and the catch can produce an audible notification. The port can further include a slot on the valve wherein the slot has a lock for locking the perforator.

In a ninth embodiment, a method for establishing flow between a container with a port and an administration set includes: (i) providing a valve having a shaft, wherein the valve is sealed to the container; (ii) providing a perforator in the shaft of the valve; (iii) rotating a first wing and a second wing toward each other, wherein the first wing and the second wing are diametrically opposed and attached to the valve, and further wherein the first wing and the second wing contact the perforator; (iv) piercing the container with the perforator; and (v) locking the first wing and the second wing. The method can further include locking the perforator to the valve.

In a tenth embodiment, an access port is provided and includes: (i) a shell; (ii) a perforator located within the shell, the perforator including an end configured to pierce a medical fluid container; and (iii) a safety tab connected to the perforator, the safety tab preventing the perforator from piercing the medical fluid container, the safety tab manually removable to enable the perforator to pierce the medical fluid container.

In this tenth embodiment: (i) the shell can include a portion configured to attach to a valve sealed to the fluid container; (ii) if the end of the perforator is a first end, the perforator can include a second end configured to connect to a fluid carrying tube; (iii) a protective cap can be placed on the second end; and (iv) wherein at least one arm can be connected pivotally to the shell, the arm contacting the perforator, so that when pivoted the arm moves the perforator with respect to the shell.

Also in this tenth embodiment, the safety tab can include a ring that initially prevents the perforator from piercing the fluid container. The ring can connect to the perforator via a plurality of frangible fixtures. The geometry of each fixture can be configured so that a tear or tamper resistance caused by the fixture is most maximal in a direction at least substantially parallel with the perforator.

Also in this tenth embodiment, a flange can be extended from the perforator, wherein the ring is connected to the flange via a plurality of frangible fixtures. Here, the geometry of each fixture can be configured so that a tear resistance caused by the fixture is most minimal in a direction at least substantially parallel with the flange. The flange can be sized to fit through the shell, and wherein the ring connected to the flange is sized not to fit through the shell. The safety tab can include a handle connected to the ring, the handle configured to be manually grasped and pulled.

In an eleventh embodiment, a medical fluid container assembly is provided and includes: (i) at least one flexible film forming a fluid tight container; and (ii) an access port configured to be coupled to the container, the access port including a safety tab preventing the film from being pierced, the safety tab including a plurality of frangible fixtures, the fixtures collectively providing a suitably high tamper resistance force, the fixtures individually providing a suitably low tab removal force.

In this eleventh embodiment, the access port can include a perforator and a shell, wherein the safety tab is connected removably to the perforator, and the shell is configured to be connected to the container. The assembly can be provided to a customer in an unassembled manner in which the access port is disconnected from the container. The container can hold a medical fluid selected from the group consisting of: dialysate, saline, nutrition solutions, irrigation solutions, parenteral solutions, oncological solutions or any other medical fluid. At least one of the fixtures can: (i) have a tetrahedron shape; (ii) be configured to narrow towards a point contact frangible interface; (iii) connect the safety tab to the perforator, wherein the safety tab abuts against the shell to prevent the perforator from piercing the film; and (iv) provide a portion of an overall tamper resistance force.

In a twelfth embodiment, an access port is provided and includes: a perforator including an end configured to pierce a medical fluid container; and a shell positioned outside of the perforator, the shell including a body and a pair of arms (i) connected hingedly to the body and (ii) extending angularly away from the body toward the piercing end of the perforator, the shell further including members each having a first end connected hingedly to one of the arms and a second end abutting the perforator, the members operable to push the perforator towards the medical fluid container when the arms are pushed towards the body of the shell.

In this twelfth embodiment, the members are each configured to do at least one of: (i) connect to a middle part of one of the arms and (ii) abut a flange extending from the perforator. The perforator and the shell can be configured to provide at least one of: (i) audible feedback when the perforator is moved with respect to the shell; (ii) tactile feedback when the perforator is moved with respect to the shell; and (iii) a locked engagement after the perforator has been moved to a piercing position with respect to the shell.

It is, therefore, an advantage of the present invention to provide a formed, filled, sealed solution container, port and method for establishing flow between the container and an administration set that may be operated with a single hand.

Another advantage of the present invention is to provide a formed, filled, sealed solution container, port and method for establishing flow between the container and an administration set that produces an audible notification when the access port is fully engaged.

Yet another advantage of the present invention is to provide a formed, filled, sealed solution container, port and method for establishing flow between the container and an administration set that provides a visible notification when the access port is fully engaged.

A further advantage of the present invention is to provide a formed, filled, sealed solution container, port and method for establishing flow between the container and an administration set wherein the access port excludes touch and air-borne contaminants.

A still further advantage of the present invention is to provide a formed, filled, sealed solution container, port and method for establishing flow between the container and an administration set wherein the access port provides a design with an activation mode and where the position of the fingers and/or hand of the user is straightforward.

Another advantage of the present invention is to provide a formed, filled, sealed solution container, port and method for establishing flow between the container and an administration set wherein the access port reduces the force required to access the container.

Yet another advantage of the present invention is to provide a formed, filled, sealed solution container, port and method for establishing flow between the container and an administration set wherein a perforator may not be withdrawn from the container.

A further advantage of the present invention is to provide a formed, filled, sealed solution container, port and method for establishing flow between the container and an administration set wherein the access port reduces the forces required to penetrate the container.

A still further advantage of the present invention is to provide a formed, filled, sealed solution container, port and method for establishing flow between the container and an administration set wherein the access port allows for a choice of different raw materials for the perforator and the valve.

Still a further advantage of the present invention is to provide an access port connectable to a medical fluid bag, wherein the access port includes a safety tab that prevents inadvertent puncturing of the bag until removed, after which the bag can be punctured.

Yet a further advantage of the present invention is to provide visual indication of whether a medical fluid bag is or is not able to be punctured by an access port.

Moreover, it is an advantage of the present invention to provide an access port with a safety tab, wherein the tab provides an effective inhibitor against inadvertent puncturing of the bag and is nevertheless relatively easy to remove.

Additional features and advantages of the present invention are described in, and will be apparent from, the detailed description of the presently preferred embodiments and from the drawings.

BRIEF DESCRIPTION OF THE FIGURES

FIG. 2A illustrates a perspective view of an access port in an embodiment of the present invention.

FIG. 4B illustrates a perspective view of an access port in an embodiment of the present invention.

FIG. 4C illustrates a perspective view of an access port in an embodiment of the present invention.

FIG. 5A illustrates a front view of an access port in an embodiment of the present invention.

FIG. 5C illustrates a cross-sectional view of a perforator and an 0-ring of an access port in an embodiment of the present invention.

FIG. 6 is a perspective view of one embodiment of a medical fluid container, valve and access port with a safety tab of the present invention.

DETAILED DESCRIPTION OF THE INVENTION

The present invention generally relates to a container with an access port and a method for establishing flow between the container and an administration set. The port may seal to the container and may puncture the container to provide access to the solution in the container. The solution may be withdrawn from the container to an interior of the port wherein a line connecting the port to the administration set may further withdraw the solution to the administration set.

Figure 1:
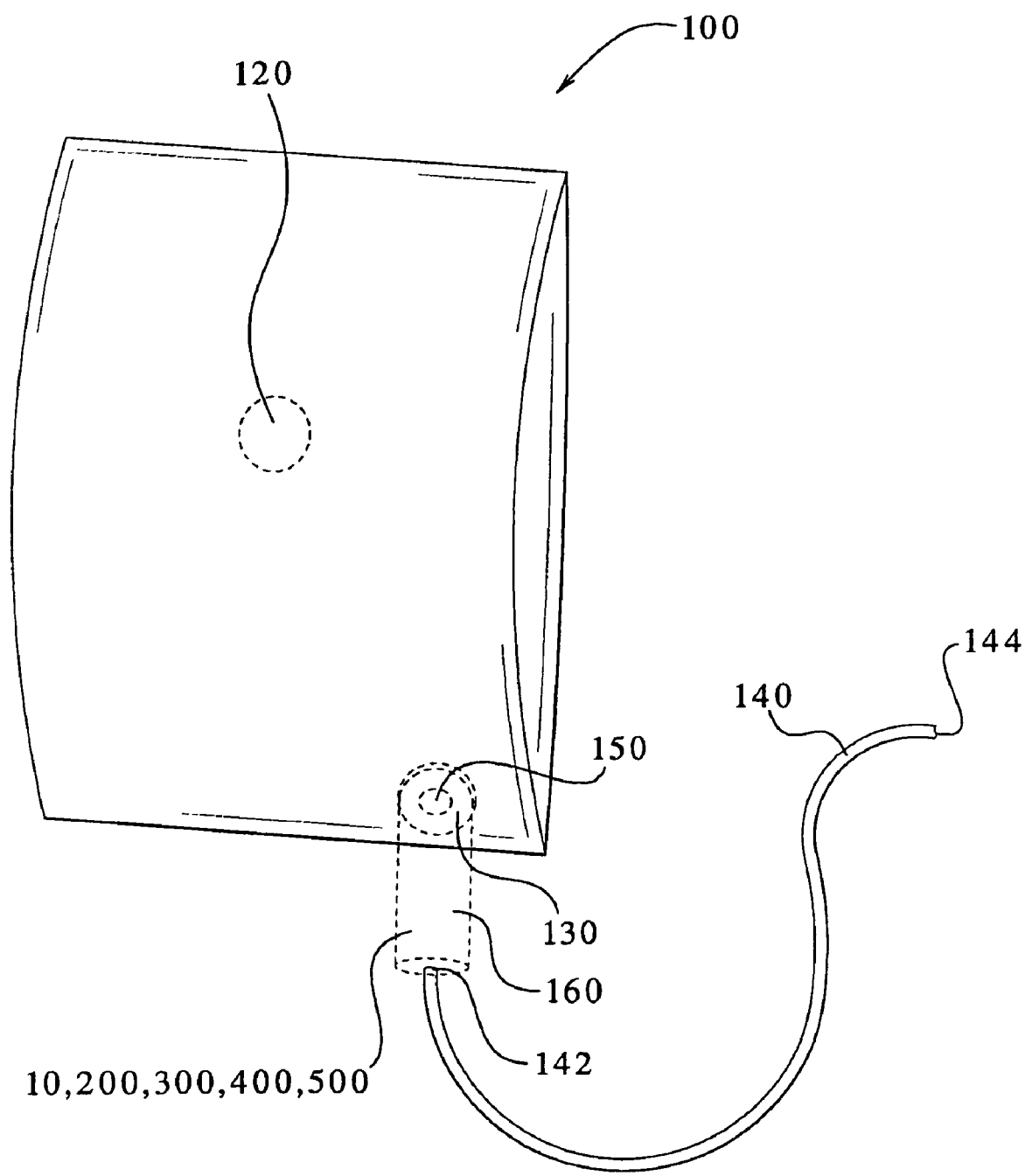
FIG. 1 illustrates a perspective view of a container with an access port in an embodiment of the present invention.

Referring now to the drawings wherein like numerals refer to like parts, FIG. 1 illustrates a container 100a. The container 100a may be constructed by folding a film and sealing the film along the sides of the film. The folded film may then be filled with a medical solution and then sealed along the top to form a sealed, fluid-filled container. The container 100a may be constructed from a transparent material, such as, for example, Clearflex™ The container 100a may include solutions, such as, for example, a peritoneal dialysis solution. The container 100a may have an input 120 for receiving an additive. The input 120 may have an injection site protected by a plastic cap.

The container 100a may further have an output 130 for providing the medical solution to a patient. The output 130 may have a liner constructed from an elastomeric material, such as, for example, film 150, interposed between an end surface of the output 130 and an access port 160. The film 150, of the output 130 may be engaged by the access port 160 to establish a fluid connection between the access port 160 and the container 100a. Further, an administration line 140 may connect the container 100a to an object, such as, a patient, other bag, or the like. A fluid path may be established by connecting the administration line 140 to the container 100a and the object. The administration line 140 may be connected to the container 100a by an access port 160. As illustrated in FIG. 1, container 100a is operable with different access ports, such as access ports 10, 200, 300, 400 and 500 described herein.

Referring now to FIG. 2A, an access port 200 is generally illustrated. To access the solution in the container 100a, the access port 200 may establish flow of fluid through the output 130 from the container 100a to the administration line 140. In an embodiment of the present invention, the access port 200 may have a valve 202, a cock 204, a plunger 206, and a gasket 208. The plunger 206 of the access port 200 is shown in a standby position.

Figure 2B:
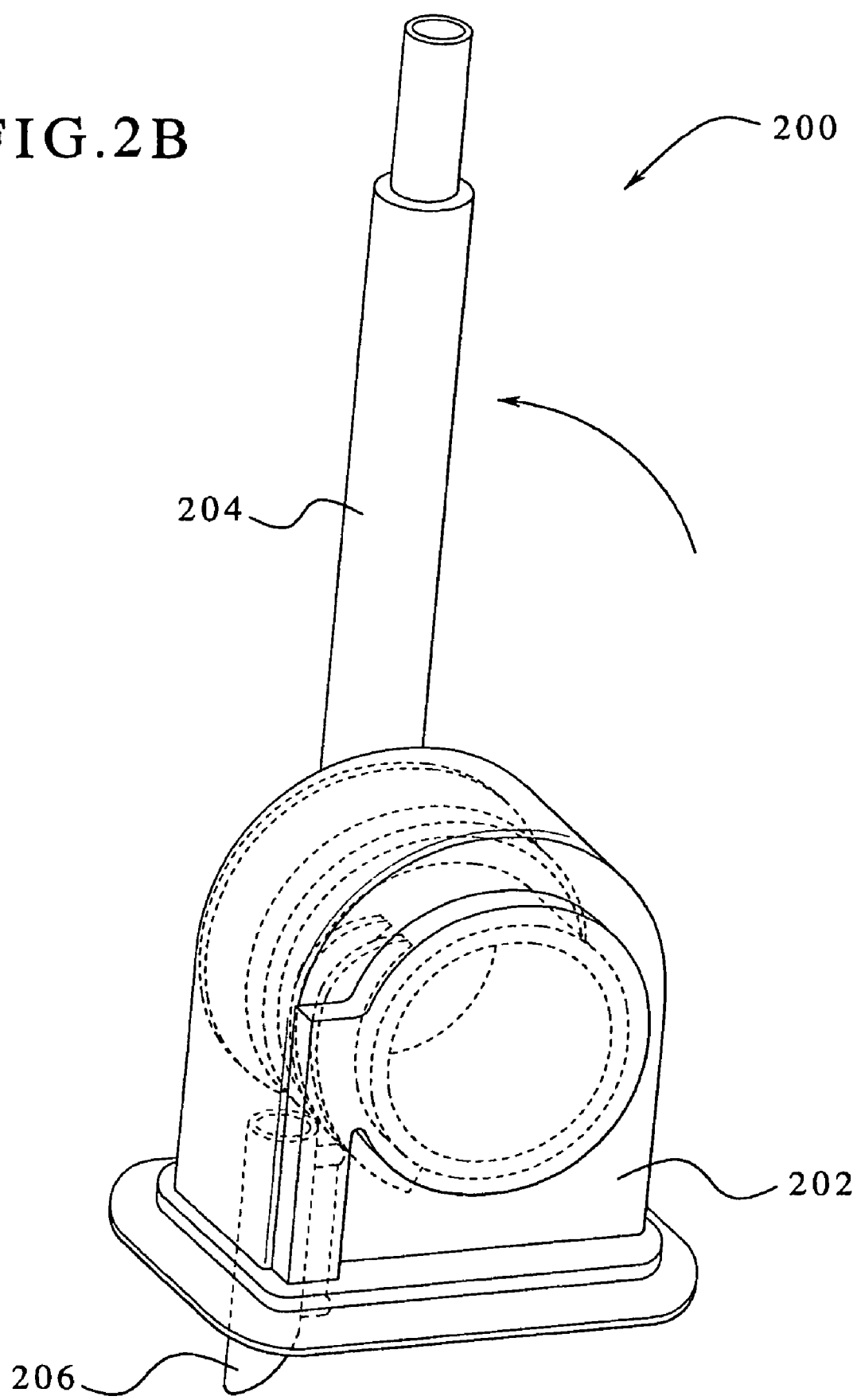
FIG. 2B illustrates a perspective view of an access port in an embodiment of the present invention.

Referring to FIG. 2B, the plunger 206 of the access port 200 is shown in an activated position. By rotating the cock 204 from a substantially horizontal position (standby position) to a substantially vertical position, the access port 200 may be activated. The rotation of the cock 204 may force the plunger 206 to lower and/or to pierce the container 100a.

Figure 2C:
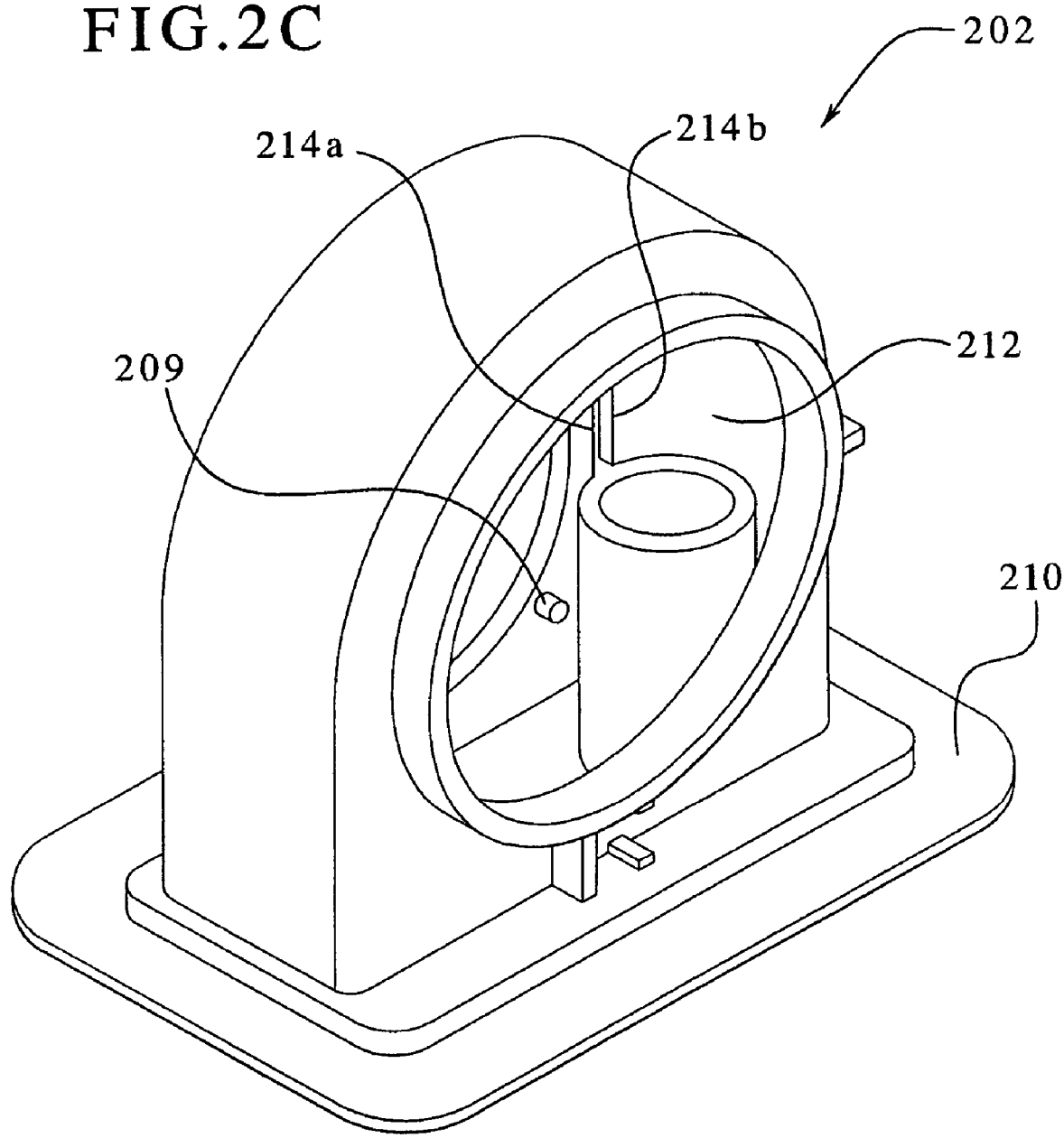
FIG. 2C illustrates a perspective view of a valve of an access port in an embodiment of the present invention.

Referring to FIG. 2C, the valve 202 may be molded from, for example, a blend that ensures a number of different functions, such as, for example, an E modulus of approximately 900 MPa. The valve 202 may be surrounded by a peripheral foot section 210 that may be sonically sealed onto the film 150 of the solution container 100a. The foot section 210 may prevent leakage of the medical solution from the container 100a. The valve 202 may provide a cylindrical housing 212 having two shoulders 214a and 214b. The cock 204 may be axially guided by the two shoulders 214a and 214b of the cylindrical housing 212. On an internal side of the valve 202, internal catches 209 may be designed to establish a standby position and an activated position of the plunger 206 as shown in FIGS. 2A and 2B, respectively. Preferably, locks may be provided to lock the plunger 206 in a standby or an activated position.

Referring again to FIG. 2A, the plunger 206 of the access port 200 is shown in a standby position, i.e. the cock 204 is in a substantially horizontal position, and the plunger 206 is enclosed within the valve 202. Referring to FIG. 2B, the access port 200 with the plunger 206 locked in an activated position is illustrated, i.e. the cock 204 is in a substantially vertical position, and the plunger 206 is protruding from the valve 202. Further, the valve 202 may include a latch that may lock the cock 204 in the activated mode. Locking the cock 204 may generate a sound thereby providing an audible notification that the cock 204 has been locked.

Figure 2D:
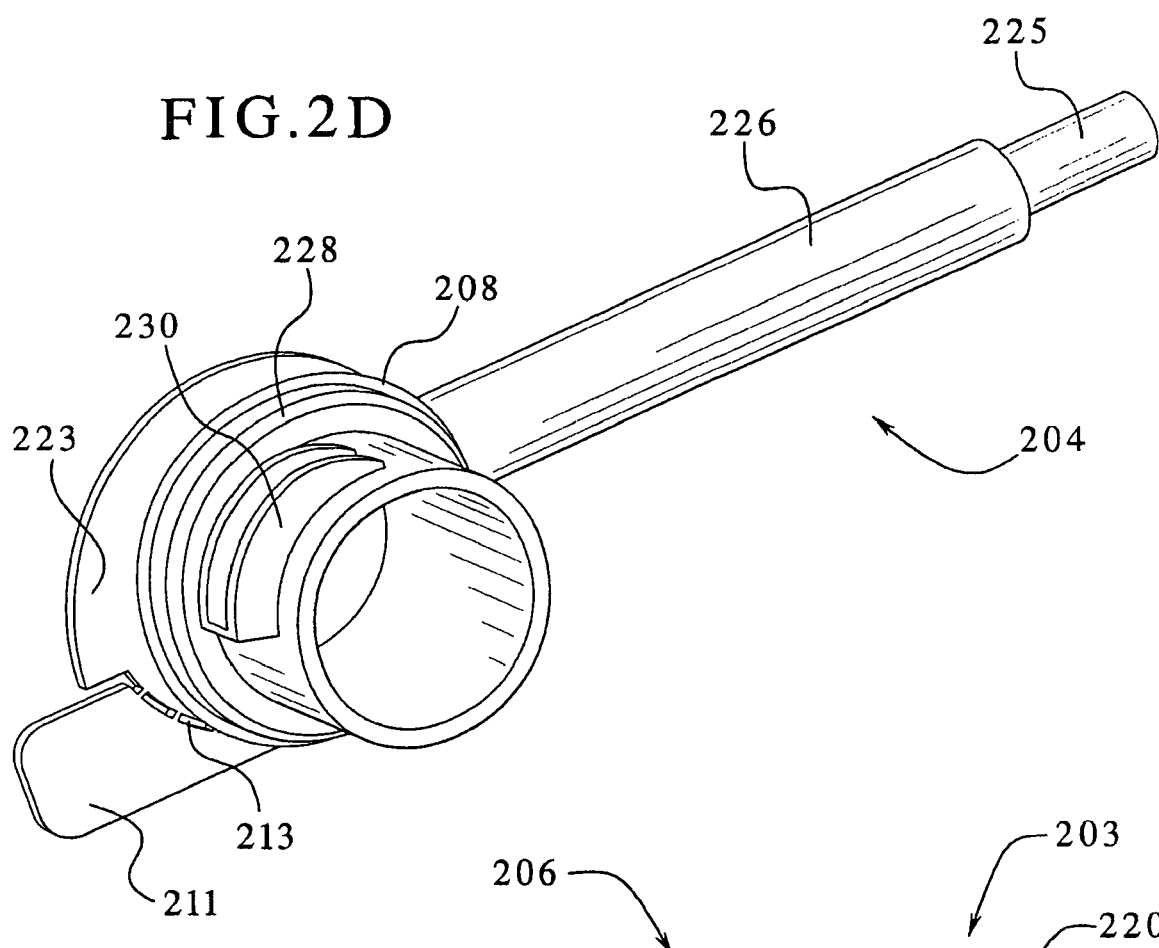
FIG. 2D illustrates a perspective view of a cock of an access port in an embodiment of the present invention.
Figure 2E:
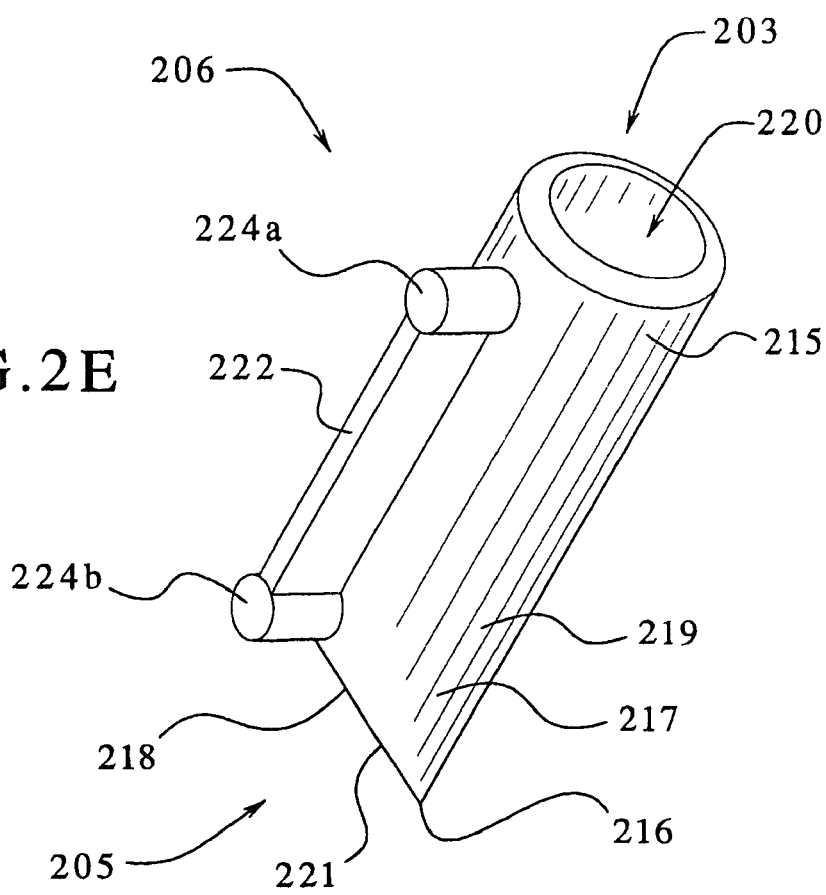
FIG. 2E illustrates a perspective view of a plunger of an access port in an embodiment of the present invention.

Referring to FIG. 2E, the plunger 206 may be molded from a blend having, for example, an E modulus greater than 1500 MPa. The plunger 206 may provide at least three functions. First, the plunger 206 may puncture the film 150 of the container 100a and may open an access to the solution. A tip 216 of the plunger 206 may be designed to puncture and/or to tear the film 150 located below the peripheral foot section 210 of the valve 202. More specifically, the plunger 206 may be shaped from a hollow cylinder that tapers from a first end 203 to a second end 205 of the plunger 206. An outside surface 215 of the plunger 206 may have a first cut 217 and a second cut 219 angularly disposed to each other at the second end 205 of the plunger 206 to define the tip 216. The second end 205 with the first cut 217 and the second cut 219 define a tri-slope bevel 218 of the tip 216. Further, the design of the tri-slope bevel 218 of the tip 216 of the plunger 206 may generate minimal friction forces.

Second, the plunger 206 may allow solution flow from the container 100a into the valve 202 through a hollowed shaft 220 of the plunger 206. Third, the plunger 206 may have an axial and external beam 222 that may guide the plunger 206 into the valve 202 during activation of the access port 200. The axial and external beam 222 may have two knobs 224a and 224b. The axial and external beam 222 and the two knobs 224a and 224b may guide the plunger 206. The knobs 224a and 224b may prevent rotation of the plunger 206. Further, the knobs 224a and 224b may position the plunger 206 into both a standby position and an activated position. Preferably, locks may be provided to lock the plunger 206 in a standby or an activated position.

Referring to FIG. 2D, the cock 204 may be molded from a blend having, for example, an E modulus of approximately 1000 MPa. The cock 204 may provide an exhaust of the valve 202 allowing fluid to be emptied from the valve 202. On a path 223 of the cock 204, a tearaway tamper proof tab 211 may impede any unintentional movement of the cock 204 to impede unintentional activation of the access port 200. The tamper proof tab 211 may impede rotation of the cock 204 to lock the plunger 206 of the access port 200 in a standby position. The tamper proof tab 211 may be constructed from the same material as the cock 204. The tamper proof tab 211 may be removably attached to the cock 204. Incisions 213 between the running path 223 of the cock 204 and the tamper proof tab 211 may provide for removal of the tamper proof tab 211 from the cock 204. Of course, the tamper proof tab 211 may be removably attached to the cock 204 by other means, such as, for example, adhesive or the like.

The cock 204 may provide four functions. First, the cock 204 may create a fluid path by connecting the administration line 140 to the container 100a as shown in FIG. 1. The cock 204 may be hollowed and may have, at one of its extremities, a press fit shaft 225 for bonding to the administration line 140. Second, the cock 204 may produce a force required to pierce the film 150 of the container 100a by providing a lever 226. A hand or finger of a user may be positioned on the lever 226. Third, the cock 204 may be used as a cam. For example, the cock 204 may activate the plunger 206 by rotation of the lever 226 from a substantially horizontal position to a substantially vertical position as shown in FIG. 2B. Fourth, the cock 204 may have a gasket groove 228 and a snapping catch 230. The gasket 208 may have a ring shape. The gasket 208 may ensure the liquid-tightness of the assembly and may prevent contaminants from entering a sterile fluid path. The snapping catch 230 may allow an assembly of the cock 204 into the valve 202 without affecting the relative degree of rotation of the cock 204.

The access port 200 is assembled after the valve 202, the plunger 206, the gasket 208 and the cock 204 may be connected. Removing the tamper proof tab 211 and rotating the cock 204 substantially ninety degrees may allow for an axial stroke of the plunger 206. After the plunger 206 is activated, or fully extended, the plunger 206 may be embedded into the body of the valve 202. After the plunger 206 is embedded into the body of the valve 202, the plunger 206 may not be removed from the container 100a. Furthermore, the cock 204 may be locked into the body of the valve 202 so that rotation of the cock 204 may be prevented.

The rotation of the cock 204 may build a reactive force in the access port 200. The reactive force in the access port 200 may allow for single-handed operation. The access port 200 may enable the administration line 140 to be parallel to the sides of the container 100a in a standby position.

Figure 3A:
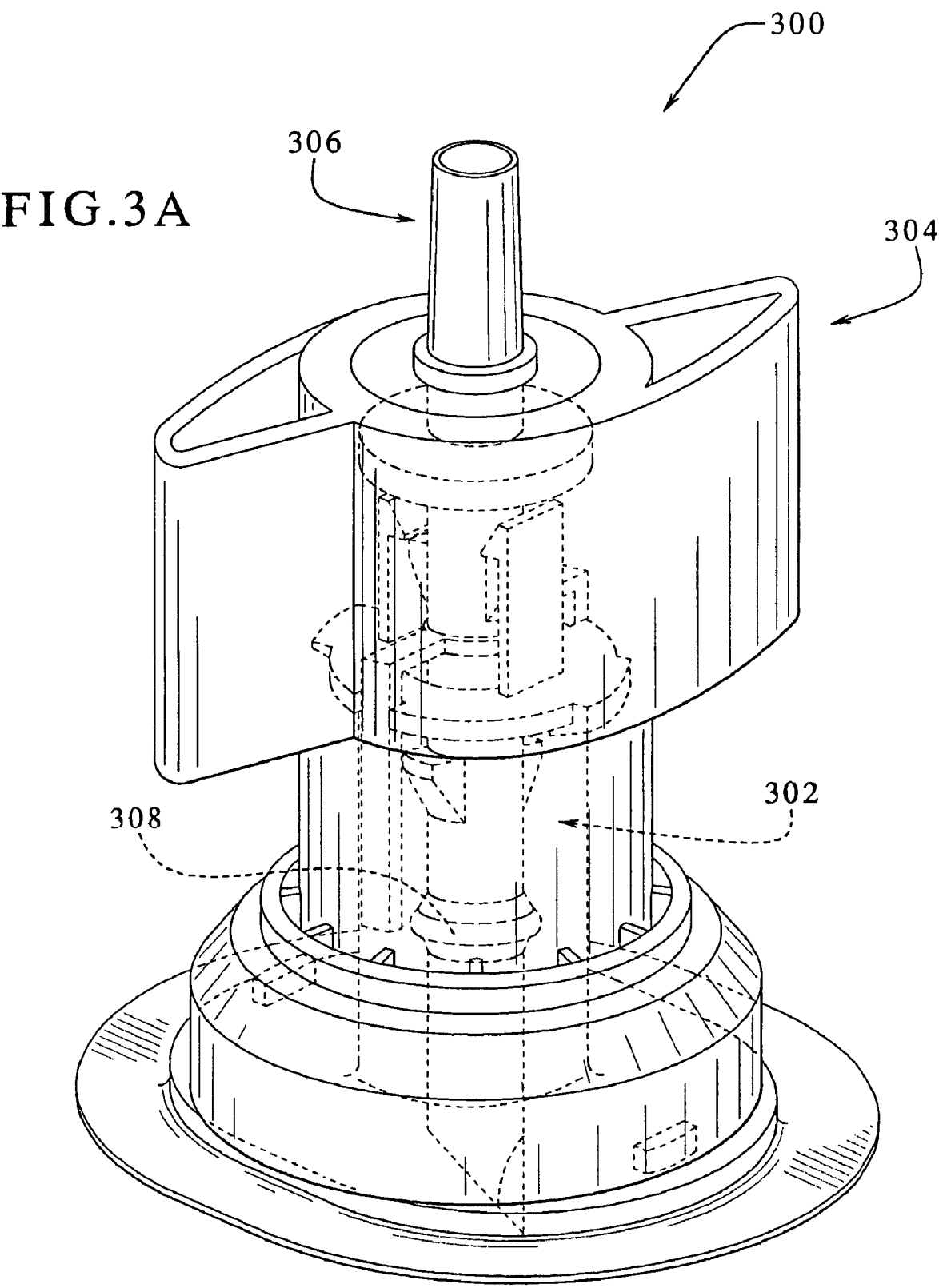
FIG. 3A illustrates a perspective view of an access port in an embodiment of the present invention.

Referring now to FIG. 3A, in another embodiment of the present invention, an access port 300 may have four different parts, a valve 302, a threaded shell 304, a perforator 306, and a gasket 308. The perforator 306 of the access port 300 is shown in a standby position. Each of the four different parts of the access port 300 will be discussed in further detail.

Figure 3B:
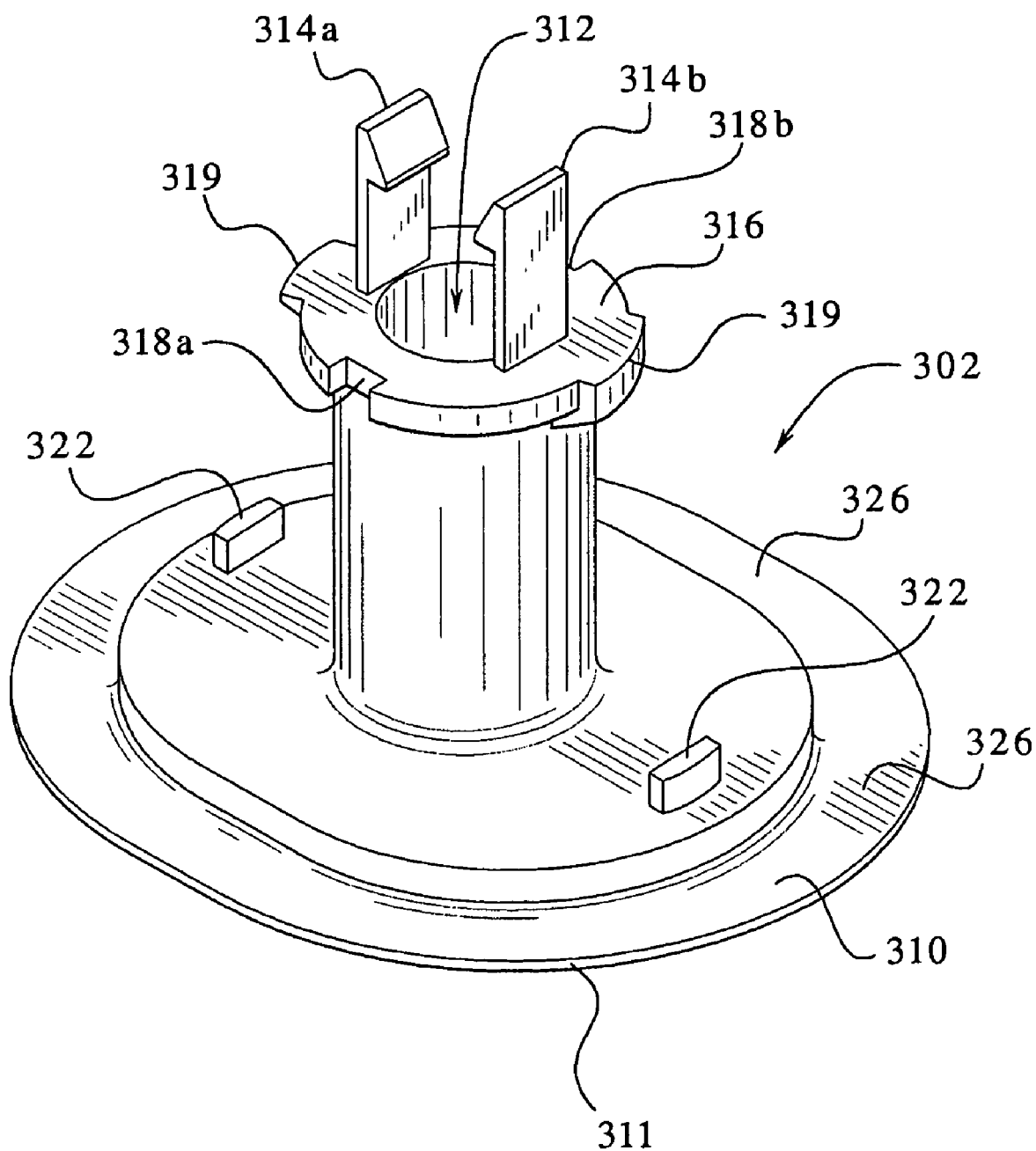
FIG. 3B illustrates a perspective view of a valve of an access port in an embodiment of the present invention.

Referring to FIG. 3B, the valve 302 may be molded from, for example, a blend having an E modulus of approximately 900 MPa that provides six functions. First, the valve 302 may have an ability to seal the access port 300 onto the film 150 of the container 100a. The valve 302 may be surrounded by a peripheral foot section 310. The peripheral foot section 310 may have a thickness 311 that is sonically sealed onto the film 150 of the container 100a. Second, the valve 302 may allow for axial guiding of the perforator 306. The valve 302 may have a cylindrical hollow shaft 312 for the axial guiding of the perforator 306. Third, the valve 302 may position the perforator 306 in a standby position and an activated position. Two cantilever beams 314a and 314b may protrude from a top 316 of the valve 302. The two cantilever beams 314a and 314b may prevent removal of the perforator 306 from the valve 302.

Figure 3C:
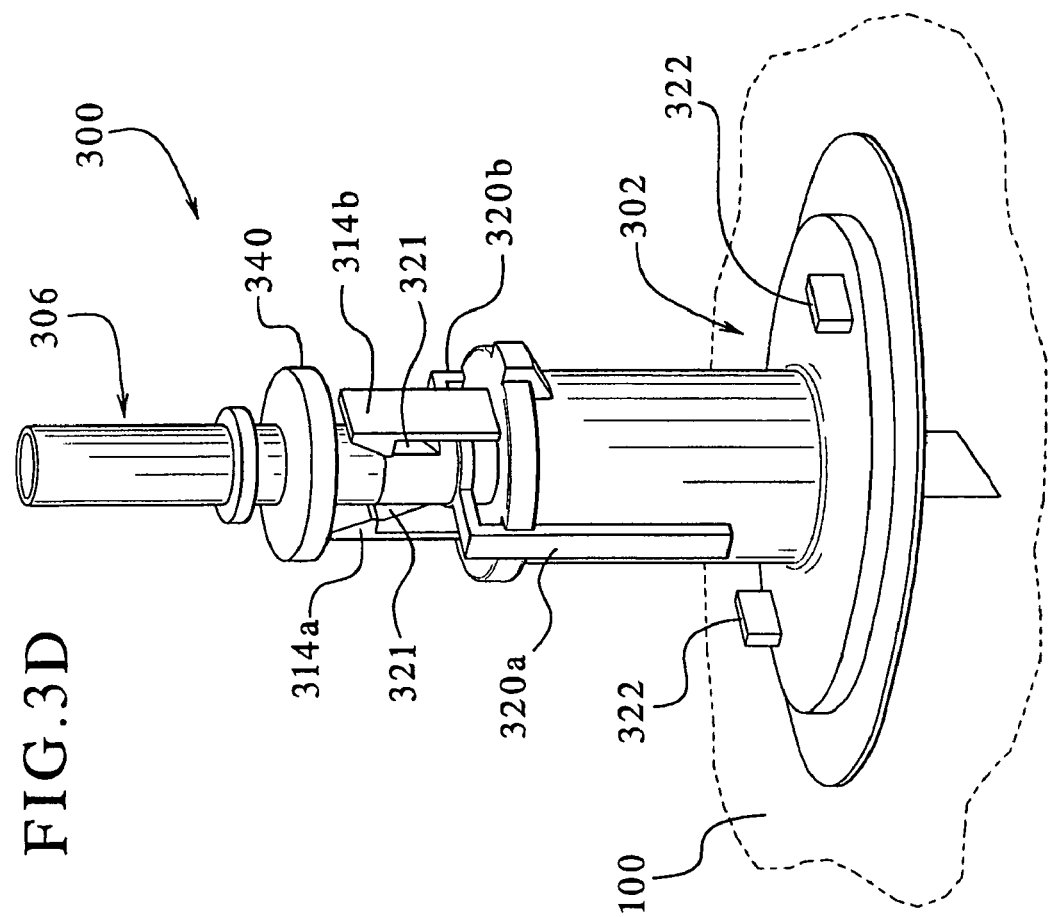
FIG. 3C illustrates a perspective view of a perforator and a valve of an access port in an embodiment of the present invention.
Figure 3D:
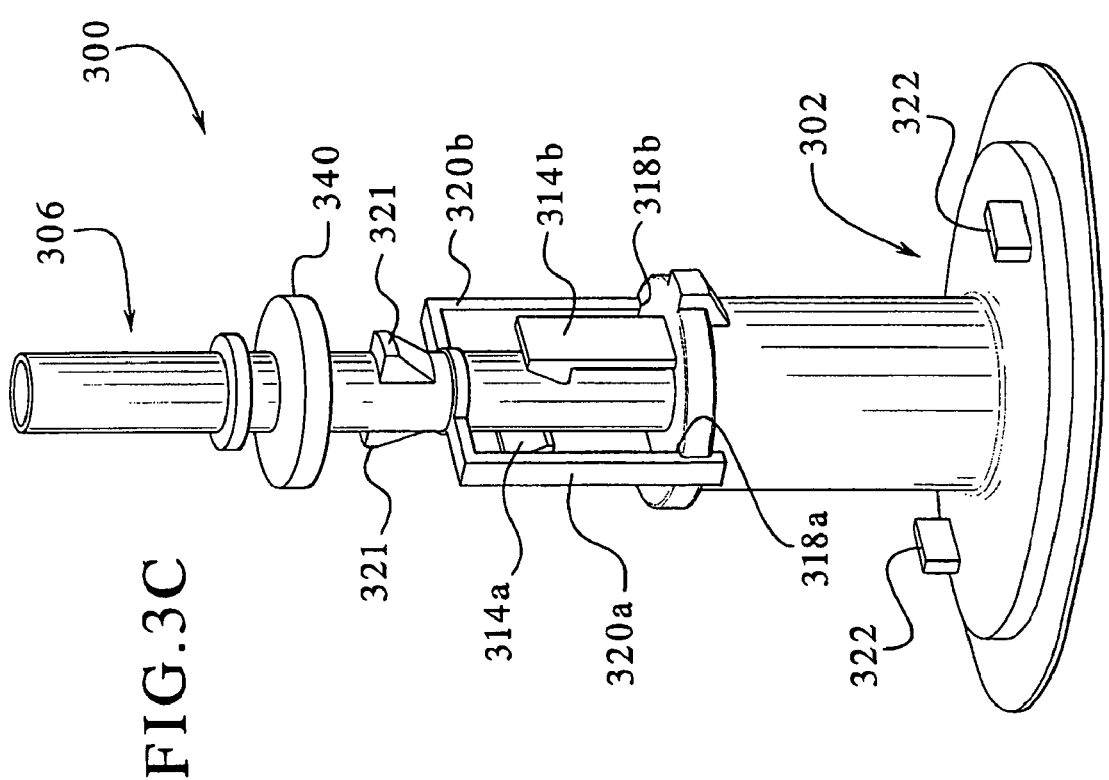
FIG. 3D illustrates a perspective view of a perforator and a valve of an access port in an embodiment of the present invention.
Figure 3E:
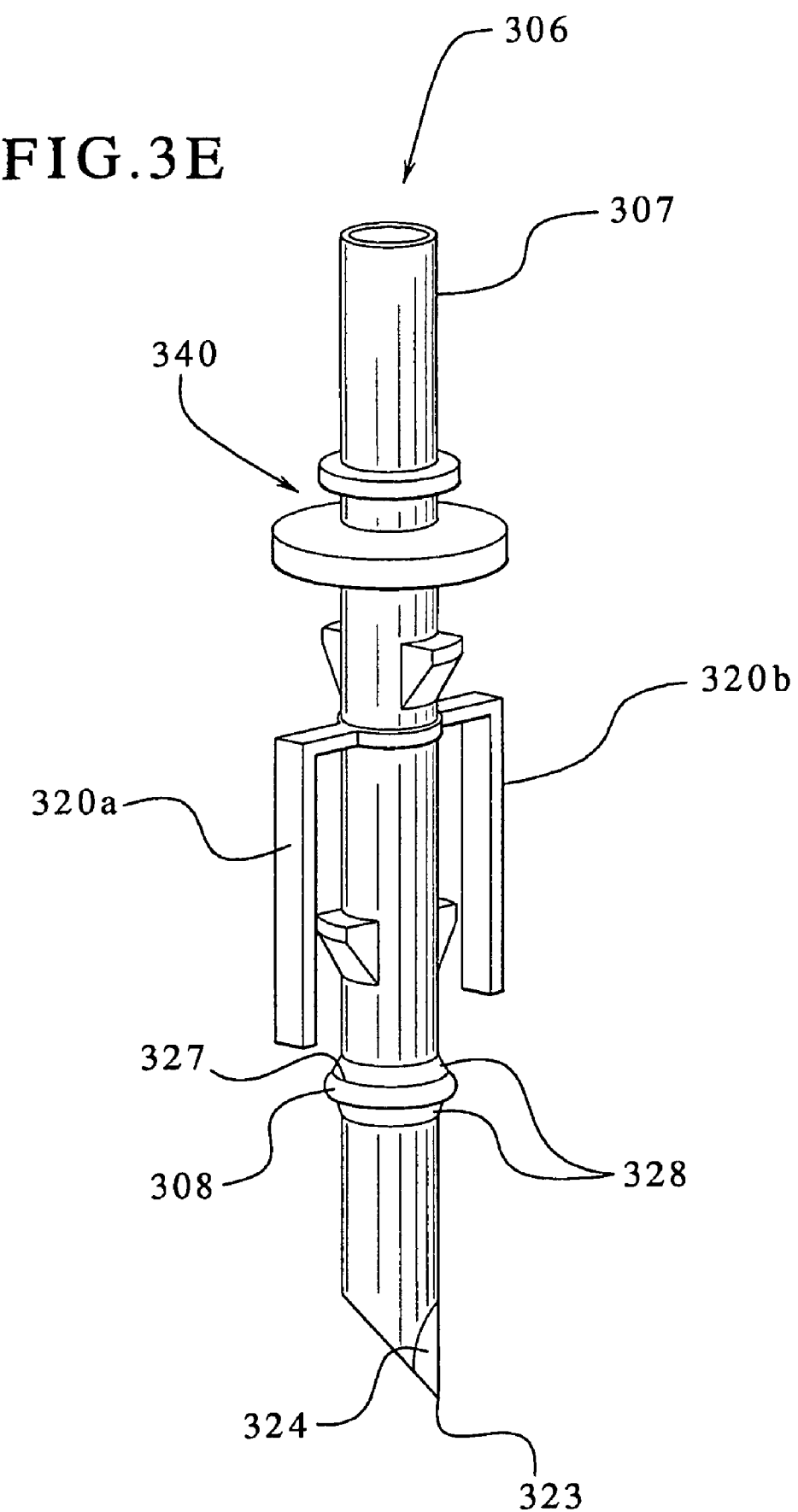
FIG. 3E illustrates a perspective view of a perforator of an access port in an embodiment of the present invention.

Referring to FIG. 3C, the two cantilever beams 314a and 314b, in an open position as shown, may hold the perforator 306 in a standby position. Fourth, the valve 302 may allow for a perforator guiding system. Two slots 318a and 318b are provided to receive arms 320a and 320b of the perforator 306. The arms 320a and 320b are shown in FIGS. 3C, 3D and 3E. The slots 318a and 318b may prevent rotation of the perforator 306 in the valve 302. Fifth, the valve 302 may have threads 319 to guide and/or mate with the threaded shell 304. Finally, as shown in FIG. 3C, the perforator 306 may have two tabs 321 located that secure the assembly in an activated position. The two tabs 322 on the valve 302 impede the rotation of the threaded shell 304 (see FIG. 3A) either in the stand-by position or during the translation of the perforator 306 to an activated position, as shown in FIG. 3D.

Referring to FIG. 3E, the perforator 306 may be molded from, for example, a blend having an E modulus greater than 1500 MPa. The perforator 306 may have at least five functions. First, the perforator 306 may puncture the film 150 of the container 100a and may establish access to solution in the container 100a. A tip 323 of the perforator 306 may have a tri-slope bevel 324. The tri-slope bevel 324 may puncture and/or may tear the film 150 under the peripheral foot section 326 of the valve 302. Further, the tri-slope bevel 324 may generate minimal friction forces.

Second, the perforator 306 may connect the container 100a to the administration line 140. The perforator 306 may have a press fit shaft 307 to press fit and/or bond the administration line 140. The perforator 306 may be hollow. After piercing the film 150, the perforator 306 may generate the fluid path from the container 100a to the administration line 140.

Third, the perforator 306 may have axial and external beams, or cantilever beams, or the arms 320a and 320b that lock into slots 318a and 318b of the valve 302 and may impede any rotation of the perforator 306 during activation. Fourth, the perforator 306 may have a gasket groove 327, a gasket 308 and a guiding flange 328. The gasket groove 327 and the guiding flange 328, in conjunction with the cylindrical hollow shaft 312 in the valve 302, may guarantee the axial guiding and the liquid-tightness of the assembly. Further, the gasket 308 may ensure the liquid-tightness of the assembly and may prevent any contamination from entering the sterile fluid path.

Fifth, the perforator 306 may have a snap 340 that may mate the threaded shell 304 with the valve 302 in an axial position that is substantially fixed but may allow for a rotational degree of freedom.

Figure 3F:
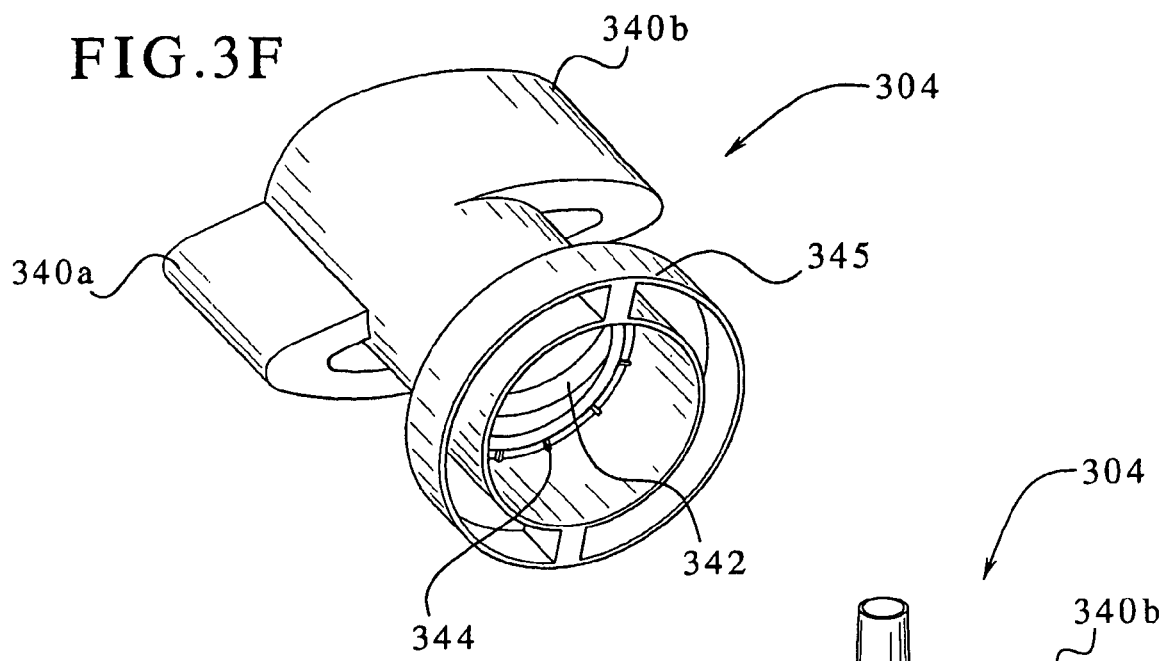
FIG. 3F illustrates a perspective view of a shell of an access port in an embodiment of the present invention.
Figure 3G:
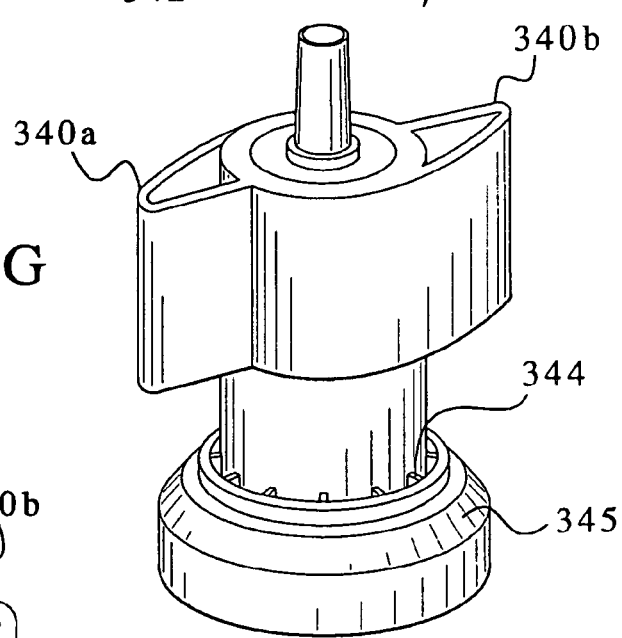
FIG. 3G illustrates a perspective view of a shell of an access port in an embodiment of the present invention.
Figure 3H:
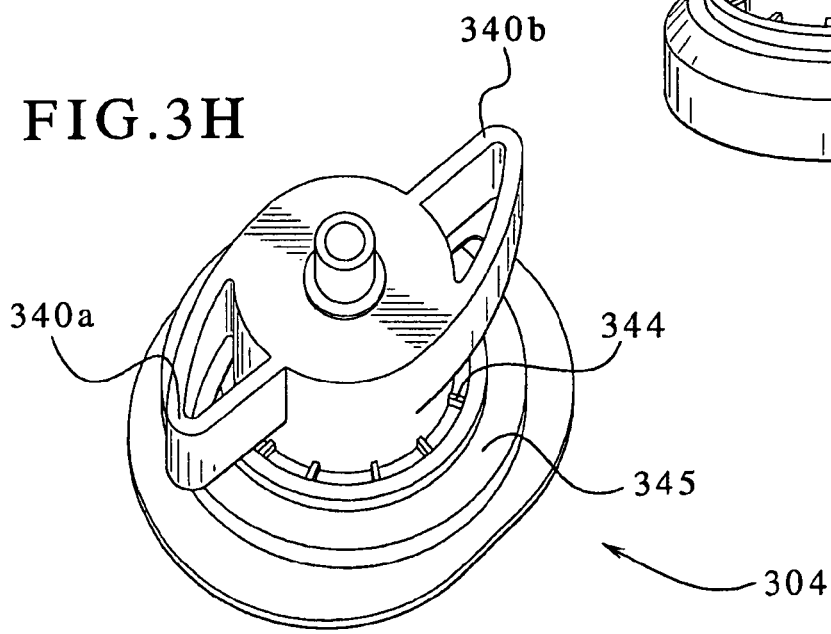
FIG. 3H illustrates a perspective view of a shell of an access port in an embodiment of the present invention.

Referring to FIGS. 3F, 3G and 3H, the threaded shell 304 may be molded from, for example, a blend having an E modulus around 1000 MPa. The threaded shell 304 may have at least three functions. First, the threaded shell 304 may reduce the forces required to pierce the film 150 of the solution container 100a by providing the two threaded wings 340a and 340b. The fingers and/or hands of a user may be positioned on the threaded wings 340a and 340b. Second, the threaded shell 304 may activate the perforator 306 during rotation by engaging internally built threads 342 in the threaded shell 304 with the threads on the valve 302.

Third, the threaded shell 304 may have a crown 345 removably attached to the threaded shell 304 wherein the crown 345 may provide evidence of tampering. More specifically, in the standby position, as shown in FIG. 3A, the crown 345 of the threaded shell 304 is located on the upper surface of the valve 302 and may be connected to the main body of the threaded shell 304 by breakable sections 344. Initiation of a screwing motion on the threaded shell 304 may tear the breakable sections 344. Broken sections 344 may provide the evidence of tampering. The breakable sections 344 may remain attached to the access port 300 after the crown 345 is detached from the threaded shell 304.

Accordingly, rotating the threaded shell 304 clockwise may tear the breakable sections 344 thereby detaching the protective crown 345. Rotating the threaded shell 304 may engage the valve 302 and the perforator 306. After detaching the protective crown 345, an axial stroke of the perforator 306 may be provided. The axial stroke of the perforator may force the perforator 306 to pierce and become embedded in the container 100a. After the perforator 306 pierces the container 100a, the access port 300 may be locked in an activated position, and withdrawal of the perforator 306 may not be possible.

The threaded shell 304 may lock onto the valve 302 such that rotation of the threaded shell 304 may be possible but the perforator 306 and the valve 302 may not be disturbed. A reactive force may build in the access port 300 due to the axial stroke of the perforator 306. The reactive force built in the access port 300 may allow for a single-handed operation during the activation of the access port 300.

Figure 4A:
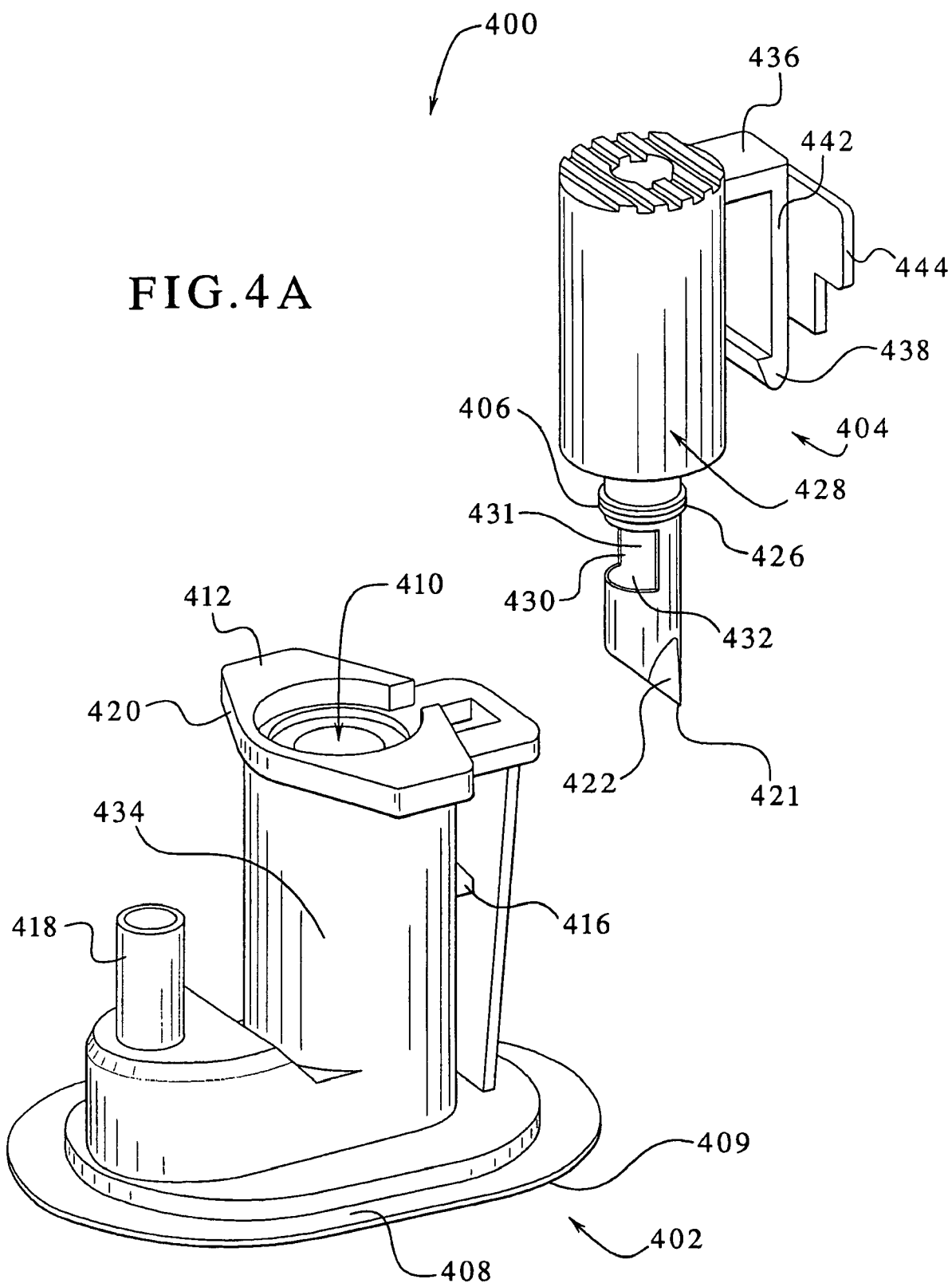
FIG. 4A illustrates a perspective view of a perforator and a valve of an access port in an embodiment of the present invention.

Referring now to FIG. 4A, in another embodiment of the present invention, an access port 400 is generally illustrated. The access port 400 may be constructed from three pieces, namely, a valve 402, a perforator 404, and a gasket 406. The valve 402 may be molded from, for example, a blend having an E modulus around 900 MPa. Further, the valve 402 may ensure at least five different functions. First, the valve 402 may have an ability to seal the access port 400 onto the film 150 of the container 100a. The valve 402 may have a peripheral section 408 with a thickness 409 and may allow sonic sealing of the peripheral section 408 onto the film 150 of the solution container 100a.

Second, the valve 402 may allow axial guiding of the perforator 404. The valve 402 may have a cylindrical hollow shaft 410 which may be surrounded by a crown 412. Third, the valve 402 may have a perforator locking system 405 in both standby and activated positions as shown in FIGS. 4B and 4C, respectively. On an external side of the valve 402, an external latch 416 may be designed to establish the standby position and the activated position. In the activated position, the access port 400 may be locked.

Fourth, the valve 402 may generate the fluid path and may connect the administration line 140 to the container 100a. The valve 402 may have a press fit shaft 418 to bond the administration line 140. Finally, the valve 402 may have a finger pad 420 which may indicate where the fingers of a user may be positioned. The finger pad 420 may concentrate forces that may be applied around the valve 402.

The perforator 404 may be molded from, for example, a blend having an E modulus greater than 1500 MPa and may provide at least six functions. First, the perforator 404 may puncture the film 150 of the container 100a to provide access to the solution in the container 100a. A tip 421 of the perforator 404 may have a tri-slope bevel 422. The tri-slope bevel 422 may be designed to puncture and tear the film 150 beneath the peripheral foot section 408 of the valve 402 with minimal friction forces. Second, the perforator 404 may have a gasket groove 426 and a guiding shroud 428. The gasket groove 426, the gasket 406 and the guiding shroud 428, in conjunction with the cylindrical hollow shaft 410 of the valve 402, may provide axial guidance and liquid-tightness of the access port 400. Third, the perforator 404 may include a blunt hollow shaft 430 from the tip 421 through a middle 431 of an axial extension of the perforator 404. Further, a window 432 in the blunt hollow shaft 430 may allow the solution to flow from the container 100a into a main body 434 of the valve 402.

Fourth, the perforator 404 may include an integral cantilever beam 436 with a catch 438 that mates with the external latches 416 designed on the valve 402. Rotation of the shaft 430 of the perforator 404 inside the valve 402 may be prevented. Further, an arm 442 on an external side of the perforator 404 may be designed to establish the perforator 404 in a standby position and an activated position as shown in FIGS. 4B and 4C, respectively. In the activated position, the access port 400 may be locked.

Fifth, the arm 442 may have a tamper proof tab 444 which may lock the perforator in a standby position and may prevent any unintended activation. The tamper proof tab 444, removably attached to the arm 442, may be removed by breaking the attachment between the tab 444 and the arm 442. Finally, the catch 438 of the perforator 404 and latches 416 of valve 402, when snapped together, may generate an audible notification and/or may also impede any further withdrawal of the perforator 404. The gasket 406 may ensure the liquid-tightness of the assembly and/or may prevent any contamination from entering the sterile fluid path.

Removing the tab 444 may allow an axial stroke of the perforator 404. After the perforator 404 is activated, the perforator 404 may be embedded into the valve 402 so that the perforator 404 may be difficult to withdraw. Due to the axial stroke of the perforator 404, reactive forces may build in the access port 400. The reactive forces in the access port 400 may provide for a single-handed operation while activating the connection and may also prevent the need for maintaining an additional container.

Referring now to FIG. 5A, in another embodiment of the present invention, an access port 500 is generally illustrated. The access port 500 may be constructed from four components, namely, a valve 502, a perforator 504, a gasket 506, and a shell 508. The perforator 504 of the access port 500 is shown in a standby position.

Figure 5B:
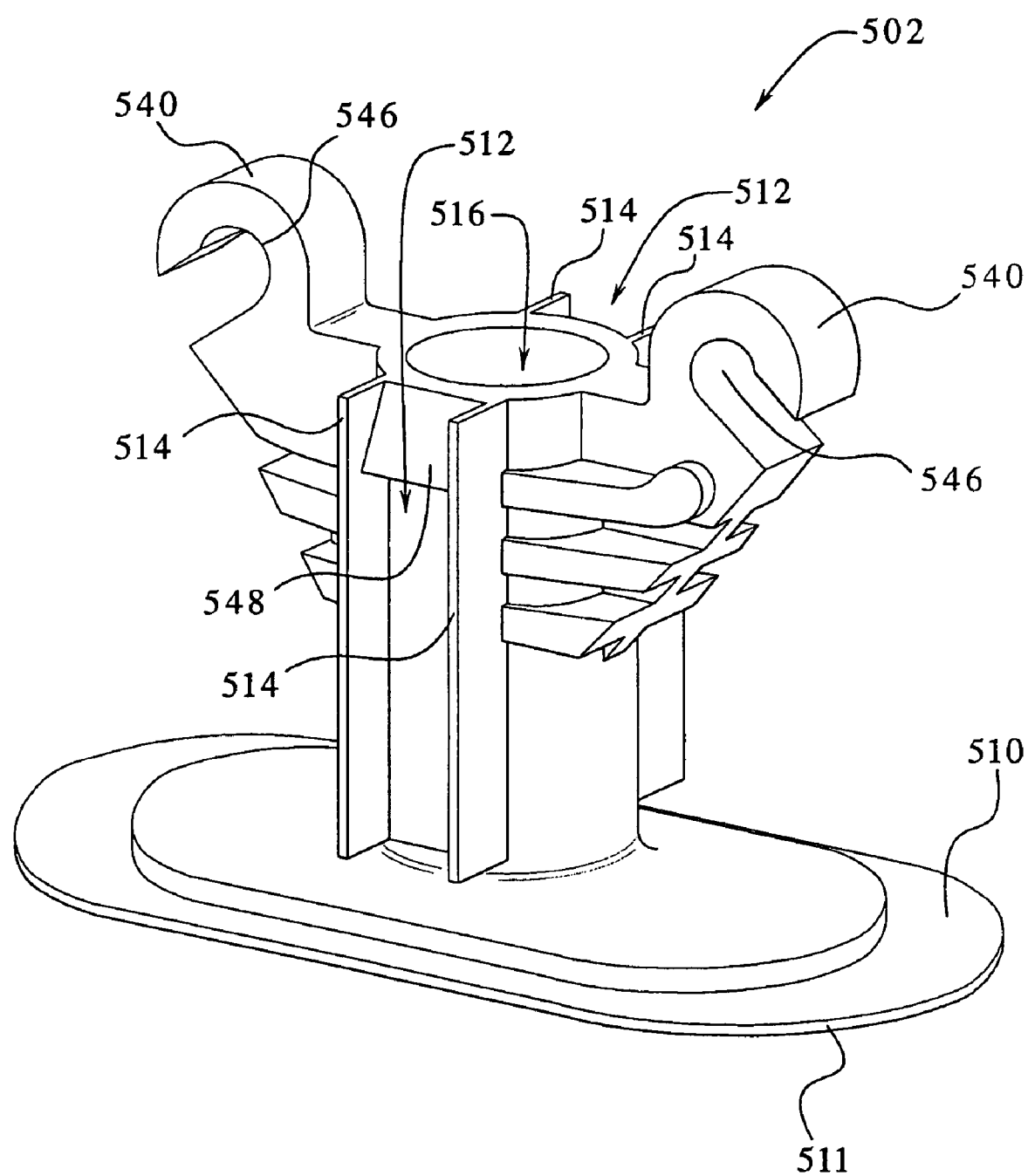
FIG. 5B illustrates a perspective view of a valve of an access port in an embodiment of the present invention.
Figure 5D:
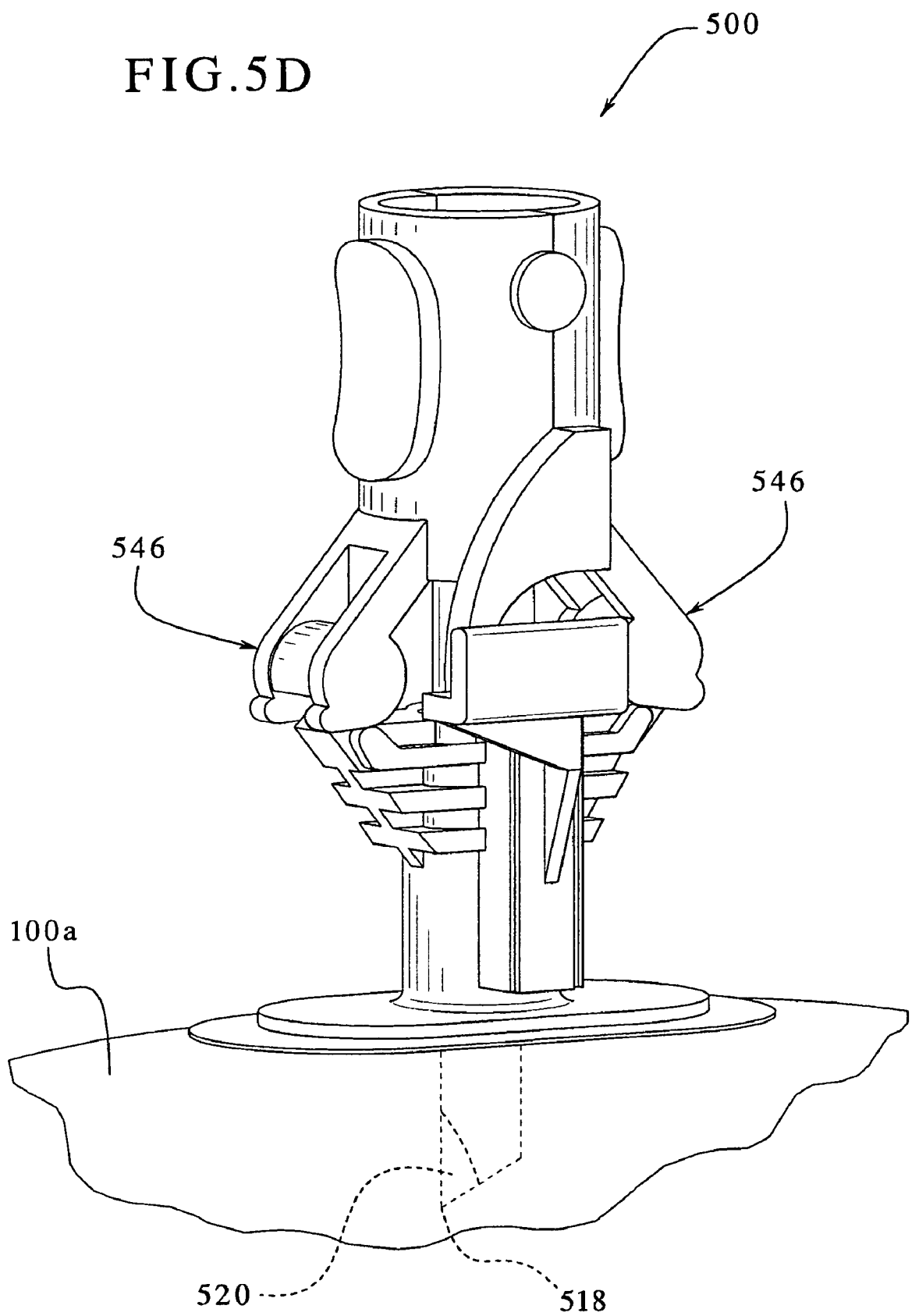
FIG. 5D illustrates a perspective view of an access port in an embodiment of the present invention.

Referring to FIG. 5B, the valve 502 may be molded from a blend, for example, having an E modulus around 900 MPa. The valve 502 may have four different functions. First, the valve 502 may seal the access port 500 onto the film 150 of the container 100a as shown in FIG. 5D. The valve 502 may be surrounded by a peripheral foot section 510 having a thickness 511 for sonic sealing of the access port 500 onto the film 150 of the container 100a. Second, the valve 502 may axially guide the perforator 504. The valve 502 may provide a cylindrical hollow shaft 516 having four axial and external flanges 514. The axial and external flanges 514 may form two axial sliding slots 516. The axial and external flanges 514 and the axial sliding slots 516 will be discussed in further detail below.

Third, the valve 502 may lock the perforator 504 in both a standby position and an activated position, as shown in FIGS. 5A and 5D, respectively. At extremities of the two axial sliding slots 512, two catches 548 may hold the perforator 504 in the standby position.

Fourth, the valve 502 may attach two shells 508. The valve 502 may have two articulations 540 diametrically opposite and at right angles of the slots 512. The articulations 540 may provide an axis 546 about which the shells 508 may rotate.

Referring to FIG. 5C, the perforator 504 may be molded from a blend, for example, having an E modulus>1500 MPa. The perforator 504 provides five functions. First, the perforator 504 may puncture the film 150 of the container 100a and may open an access to the solution of the container 100a. A tip 518 of the perforator 504 may have a tri-slope bevel 520 designed to puncture and/or tear the film 150 under the peripheral foot section 510 of the valve 502. The tri-slope bevel 520 of the tip 518 may generate minimal friction forces between the perforator 504 and the film 150.

Second, the perforator 504 may generate a fluid path between the container 100a and another object, such as, for example, a person or second container or the like. Further, the perforator 504 may connect the administration line 140 to the container 100a. The perforator 504 is hollow and has a shaft 522 that may be bonded to the administration line 140. Third, the perforator 504 may have a gasket groove 526, a gasket 506 and a guiding flange 528, which, in conjunction with the cylindrical hollow shaft 516 in the valve 502, may guarantee the axial guiding and the liquid-tightness between the perforator 504 and the valve 502. Further, the gasket 506 may ensure the liquid tightness between the perforator 504 and the valve 502 and may prevent contaminants from entering the fluid path from the container 100a to the administration set.

Fourth, the perforator 504 may have a plateau 550 that may be orthogonal to the axis of the perforator 504. Further, the perforator 504 may have two sliding grooves 552 that transform the pinching motion of the shells 508 into a force directed onto the perforator 504. Fifth, two cantilever beams 554 may mate in slots 512 of the valve 502. The cantilever beams 554, after mating with the slots 512, may prevent the rotation of the perforator 504 inside of the cylindrical hollow shaft 516 of the valve 502. More specifically, catches 548 at the extremities of the slots 512 may lock with latches 556 on the cantilever beams 554. The latches 556 of the cantilever beams 554 may lock the perforator 504 into the standby position and the activated position in the valve 502. The 2 tabs 549 (shown in FIG. 5C) lock-the perforator 504 in stand-by position before use.

Referring again to FIG. 5A, the shell 508 may be molded from a blend, for example, having an E Modulus>2000 MPa. The shell 508 may provide five functions. First, the shell 508 may provide finger pads 558. When in use, the finger pads 558 may concentrate a pinching force applied by a user. Second, the shell 508 may have an articulation 560 for mating the shell 508 to the valve 502. The articulation 560 may have two protrusions 562 that may block the position of the shell in an angular standby position, as shown in FIG. 5A.

Third, the shell 508 has a beam 564 that rests into the sliding grooves 552 on the plateau 550 of the perforator 504. The beam 564 may transform the force applied by the user into a translation motion. More specifically, a tip 566 of the beam 564 may slide into the sliding grooves 552 of the plateau 550.

Fourth, a latch and catch 568 are provided inside the shell 508 at a distal end 570 of the shell 508. When each shell 508 is snapped together, the catch and latch 568 may lock and generate a sound. The sound may provide an audible notification that the shell 508 is locked. Further, the latch and catch 568, when snapped together, may impede re-opening and/or detaching the shell 508. Fifth, the shell 508, when closed together, may form a cylinder around the activated perforator 504 in such a way that the access port 500 is shrouded as shown in FIG. 5D.

Closing the shell 508 may provide an axial stroke of the perforator 504. Detaching the shell 508 or otherwise moving the shell 508 after the shell 508 has been locked may not move the perforator 504. A ratio of a pivot length may enable the access port 500 to reduce the force required to pierce the film 150 of the container 100a. Due to the locking of the shell 508, the reactive force may increase in the access port 500. The reactive force in the access port 500 may provide single-handed operation.

The present invention may provide for a single-handed operation and may provide audible and visible notification when the tri-slope bevel has punctured the film 150 to allow solution flow from the container 100a. Further, the present invention may inhibit contamination by fully shrouding the fluid generation path to exclude touch and air-borne contamination and not allowing for the removal of the perforator or plunger from the fluid engagement position, after engagement is achieved. Still further, the present invention may reduce the amount of force needed to penetrate the film of the container.

Referring now to FIGS. 6 to 12 one embodiment of an access port with a safety tab is illustrated via perforation assembly 10, which is connected to a solution container 100b, such as a dialysate bag. Solution container 100b, like container 100a, can be constructed by folding a film and sealing the film along the sides of the film. The folded film may then be filled with a medical solution and then sealed along the top to form a sealed, fluid-filled container. Container 100b may be constructed from a transparent material, for example a Clearflex™ material. Container 100b in one embodiment includes a medication port 120 that receives a medication additive. As illustrated, medication port 120 in one implementation includes an injection site protected by a plastic cap.

Container 100b also includes a flap 110 with a reinforced hanger 112, which enables container 100b to be hung vertically if desired. Hanger 112 is placed at the top of container 100b, so that perforation assembly 10 extends downwardly enabling solution to be gravity fed and/or to aid a pump in pumping the solution.

As illustrated, container 100b is a multi-compartment container including a first compartment 114 and a second compartment 116. Compartment 114 holds a first fluid, such as an electrolyte used with peritoneal dialysis. Compartment 116 holds a second fluid, such as a bicarbonate used with peritoneal dialysis. When seal 118 is ruptured or broken, the first and second fluids mix to form the dialysate that is delivered to the patient's peritoneal cavity. One suitable multi-compartment bag is described in U.S. Pat. No. 6,663,743, assigned to the eventual assignee of the present application, the entire contents of which are incorporated herein by reference.

Container 100b includes a valved output 30, which outputs medical solution to the patient. Valve 30 in one embodiment has a liner constructed from an elastomeric material, such as, for example, the same material used for compartments 114 and 116. Perforation assembly 10 connects, e.g., snap-fits onto a port extending from valve 30. An administration line, such as tube 140 in FIG. 1, is connected to the opposite end of perforation assembly 10, which in turn is connected to an object, such as a disposable cassette, patient, other bag, etc.

Perforation assembly 10 includes a shell 12. Shell 12 includes a bottom portion 14 that snap-fits over the port extending from valve 30 sealed to solution container 100b. As seen best in FIGS. 7 to 10, bottom portion 14 of shell 12 includes a plurality of separate flanged sections 14a to 14d. The separate sections can flex to snap-fit over the port extending from valve 30 of container 100b.

Shell 12 encloses a perforator 16. Shell 12 and perforator 16 are made of any suitable medically compatible material, such as any plastic that may be sterilized via gamma radiation, ethylene oxide or steam. Specifically, suitable materials include polypropylene (PP), polycarbonate (PC), Polystyrene (PS), Polycycloxyde (POM), ABS.

Figure 9:
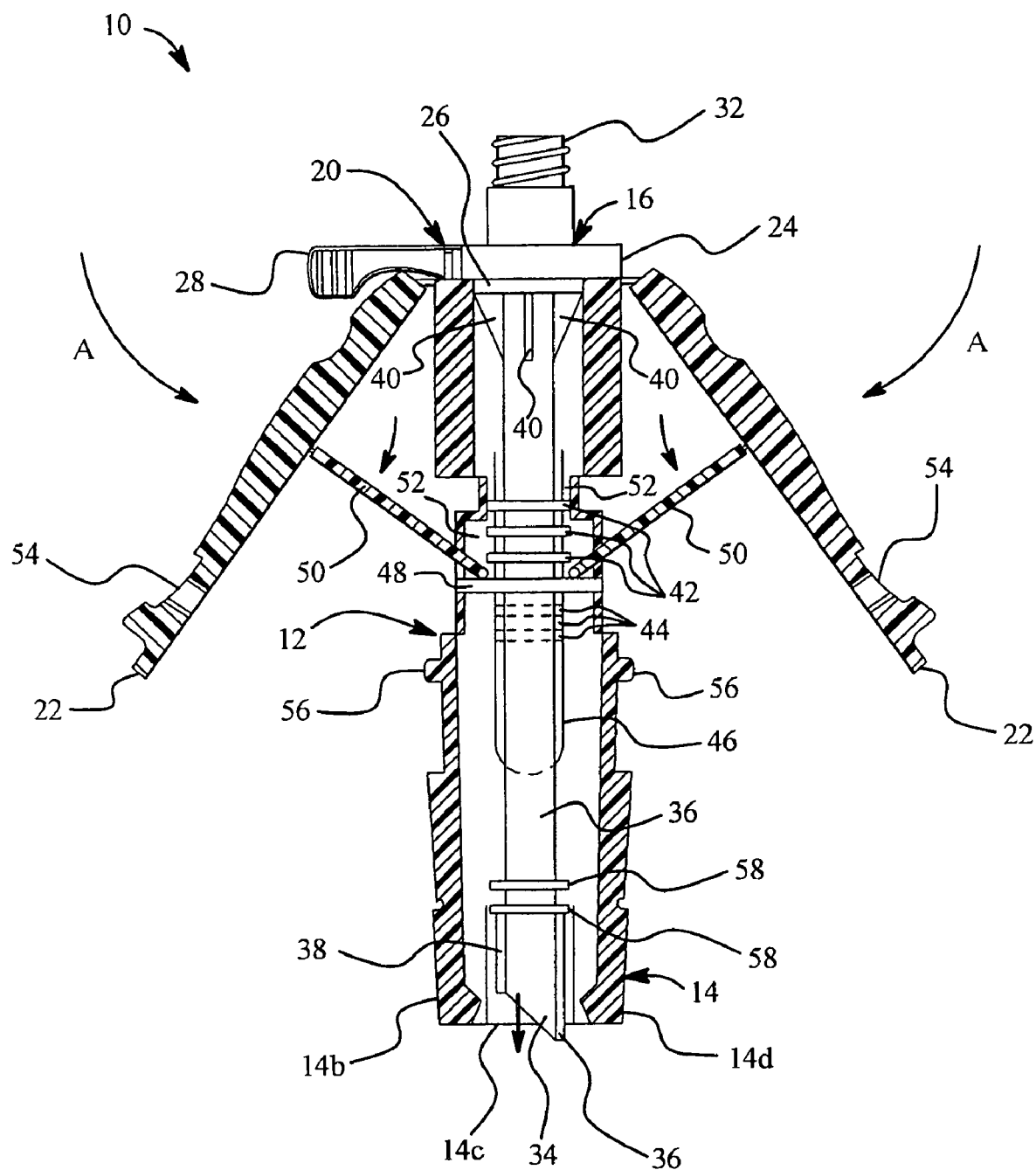
FIG. 9 is a side sectioned view of the access port with safety tab of FIGS. 6, 7 and 8 in a non-perforating position.
Figure 10:
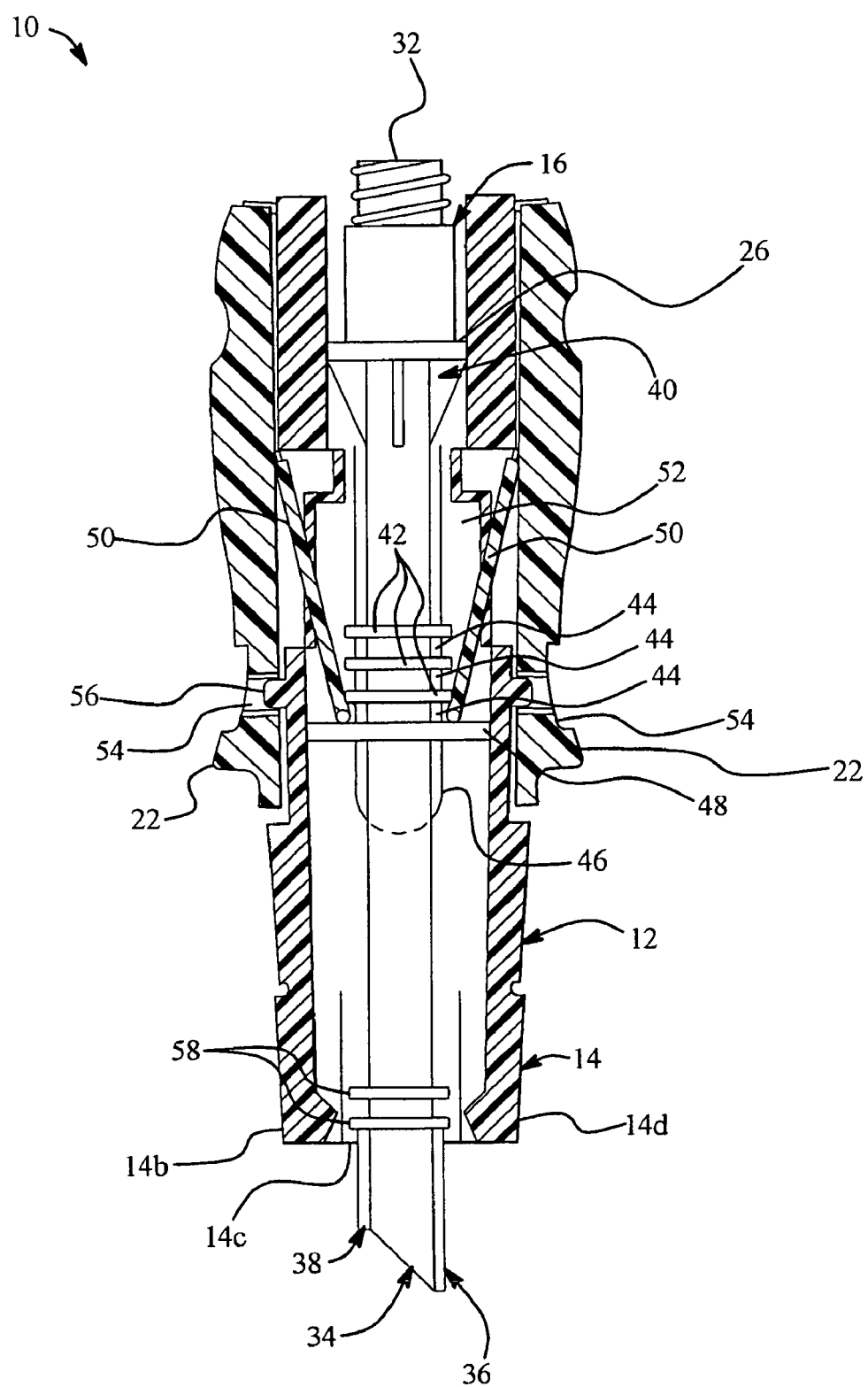
FIG. 10 is a side sectioned view of the access port of FIGS. 6, 7 and 8 (with the safety tab removed) in a perforating position.

As seen in FIGS. 9 and 10, perforator 16 includes a threaded end 32 that extends out the top of the shell 12. Threaded end 32 is configured to connect fluidly to a luer or other type of connector, which in turn connects to a tube or hose 140 (FIG. 1) of an administration set. The threads of threaded end 32 also couple to a female threaded cap 18 (FIGS. 6 to 8), which protects threaded end 32 prior to use of perforation assembly 10.

At its opposite end, perforator 16 includes a beveled tip 34. The angle of bevel may be any suitable angle, such as thirty to sixty degrees relative to a longitudinal axis of a stem 36 of perforator 16. Beveled tip 34 in one embodiment includes ribs 38, which extend longitudinally with tip 34 and provide, when engaged into slots designed inside the valve 30, means to block the rotation of the perforator 16 when Cap 18 or luer connector of administration set are screwed on and off.

A series of flanges extend radially outwardly from stem 36 of perforator 16. Beginning from the top, a circular flange 26 extends outwardly from a top portion of stem 36 of perforator 16. Flange 26 is discussed in greater detail below and is configured to attach to a removable safety tab 20. For rigidity, a plurality of gussets 40 support flange 26. Gussets 40 operate to stabilize flange 26 when safety tab 20 is torn away from perforator 16.

A series of guiding flanges 42 are provided on stem 36 below flange 26. Guiding flanges 42 are designed to ease the assembly procedure of both members 50 through the aperture 52 when the perforator 16 is inserted inside the shell 12. Although not specifically illustrated, projections 44 extending inwardly from the inside wall of shell 12 are provided (FIG. 10). These projections 44 are tapered or rounded along their upper periphery to enable a ramped engagement with drive flange 48 when perforator 16 is being moved towards a bag piercing position. Projections 44 are substantially perpendicular to the wall of shell 12 along their lower periphery to provide a locking engagement with drive flange 48 when perforator 16 has been moved or snapped to its bag piercing position.

As seen in FIGS. 6 to 10, shell 12 includes a plurality of U-shaped cutout flaps 46. Cutout flaps 46 can flex slightly relative to the remainder of shell. Projections 44 are located on the inner surface of flaps 46. As perforator 16 is moved relative to shell 12, flaps 46 flex slightly outwardly to enable drive flange 48 to move past projections 44 and eventually snap-fit between and/or around projections 44. The engagement between drive flange 48 and projections 44: (i) provide tactile and/or audible feedback to the user indicating that container 100b is being pierced and (ii) preclude the removal of perforator 16 from container 100b after the container is pierced.

Figure 7:
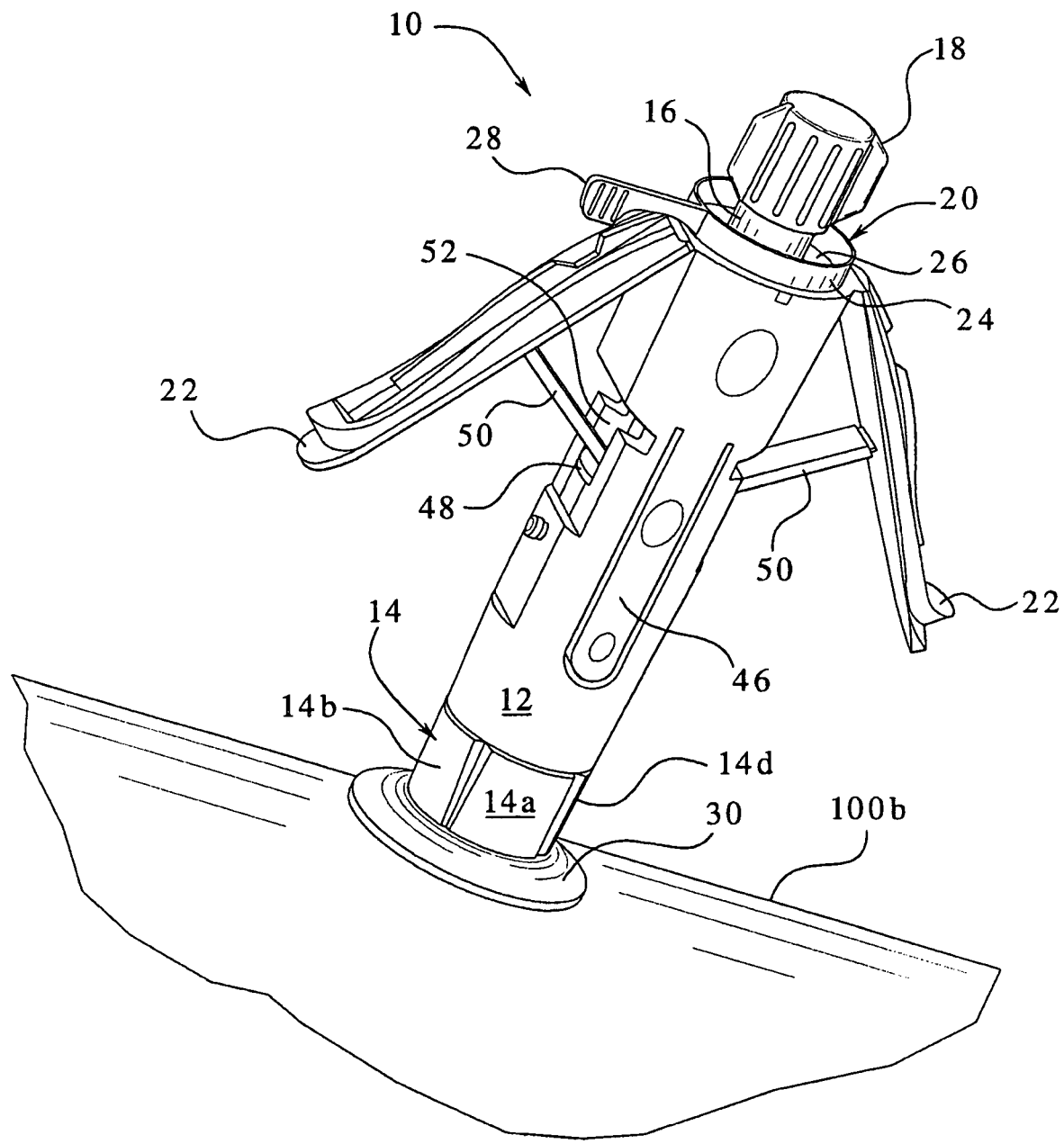
FIG. 7 is another perspective view of the fluid container, valve and access port with a safety tab of FIG. 6.
Figure 8:
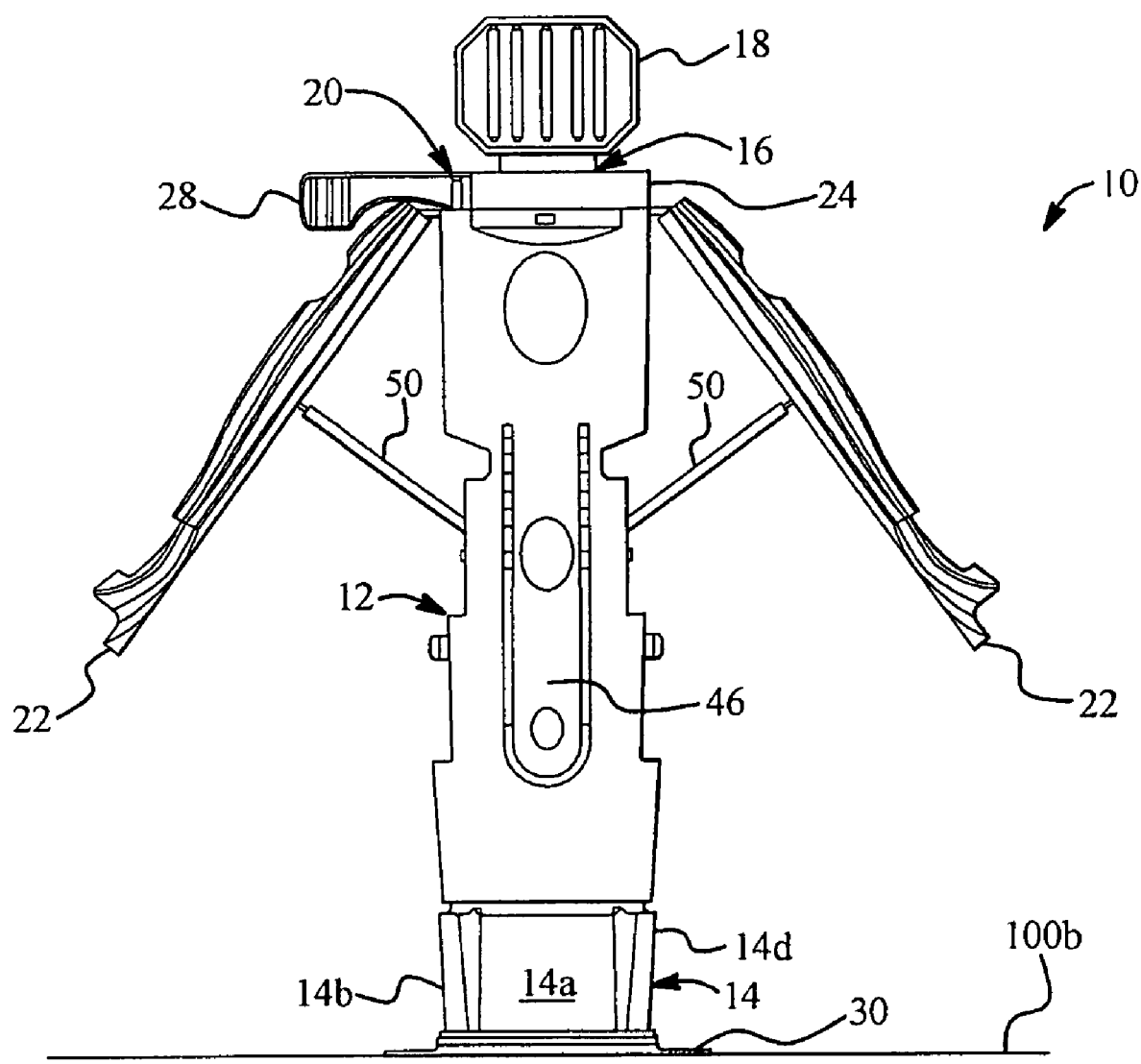
FIG. 8 is a side elevation view of the access port with safety tab of FIGS. 6 and 7.

As seen in FIGS. 7, 9 and 10, a drive flange 48 is provided on stem 36 below guiding flanges 42. Members 50 are coupled hingedly at first ends to arms 22 of shell 12. Members 50 extend through apertures 52 defined by shell 12 and contact the top surface of drive flange 48 at their second ends. Arms 22 in turn are coupled hingedly to the top of the body of shell 12.

FIGS. 9 and 10 illustrate the piercing motion of perforation assembly 10. Once safety tab 20 is removed, manual pressure is applied to the outside of arms 22. As illustrated by the arrows A of FIG. 9, the manual pressure causes arms 22 to rotate towards the body of shell 12. The rotation of arms 22 causes each member 50 to rotate towards its respective arm 22. The rotation of members 50 causes drive flange 48 and perforator 16 to move downwards (towards container 100b).

As seen in FIGS. 9 and 10, when perforator 16 is in the piercing position, arms 22 and members 50 are collapsed onto shell 12 and in substantial alignment with the body of shell 12. Perforator 16 is moved fully downwards. Flange 48 is locked between/about projections 44. Also, arms 22 define at their distal ends locking openings 54 that engage and snap-fit onto knobs 56 extending from shell 12. The friction or snap-fit engagement of openings 54 and knobs 56: (i) serves further to hold perforation assembly 10 in a locked position once piercing engagement and fluid connection is made with container 100b, (ii) provide tactile and/or audible feedback to the user indicating that container 100b is being pierced and (iii) preclude the removal of perforator 16 from container 100b after the container is pierced.

A pair of sealing flanges 58 extend from stem 36, near beveled tip 34 and ribs 38. Sealing flanges 58 generate a groove in which an appropriate sealing gasket sits (not represented). The gasket seal helps create a liquid-tight seal between the perforator 16 and the valve 30.

As seen in FIGS. 6 to 9, perforator 16 includes or is attached initially to a removable safety or tamper proof tab 20. When safety tab 20 is connected to perforator 16, a person is precluded from rotating arms 22 and members 50 inward towards shell 12 and thus from pushing perforator 16 downward with respect to the shell 12 of perforation assembly 10.

Safety tab 20 includes a ring 24 that extends around circular flange 26 of perforator 16. As discussed in more detail below in connection with FIG. 11, ring 24 is connected to the flange 26 by a plurality of frangible fixtures, such as eight fixtures. The diameter of the ring 24 is larger than the inner diameter of hollow shell 12, so that perforator 16 cannot move within the shell 12 before ring 24 of safety tab 20 is removed from flange 26. The diameter of the flange 26 is smaller than the inner diameter of hollow shell 12, so that the flange 26 of perforator 16 can move within the shell 12 after ring 24 of tab 20 is removed from flange 26.

Ring 24 of the safety tab 20 is connected also to a handle 28, which includes knurls, perforations, projections or other type of apparatus that makes handle 28 intuitive and easy to grasp and pull. Handle 28 is ergonomically configured to avoid slippage and the provide a lager grasping area away from the body of shell 12. Handle 28 may be positioned substantially vertically with respect to perforation assembly 10, substantially perpendicular or at any desired angle with respect to the assembly. The operator grabs handle 28 and tears the ring 24 from perforator 16 by rupturing the plurality of, e.g., eight fixtures.

Figure 11:
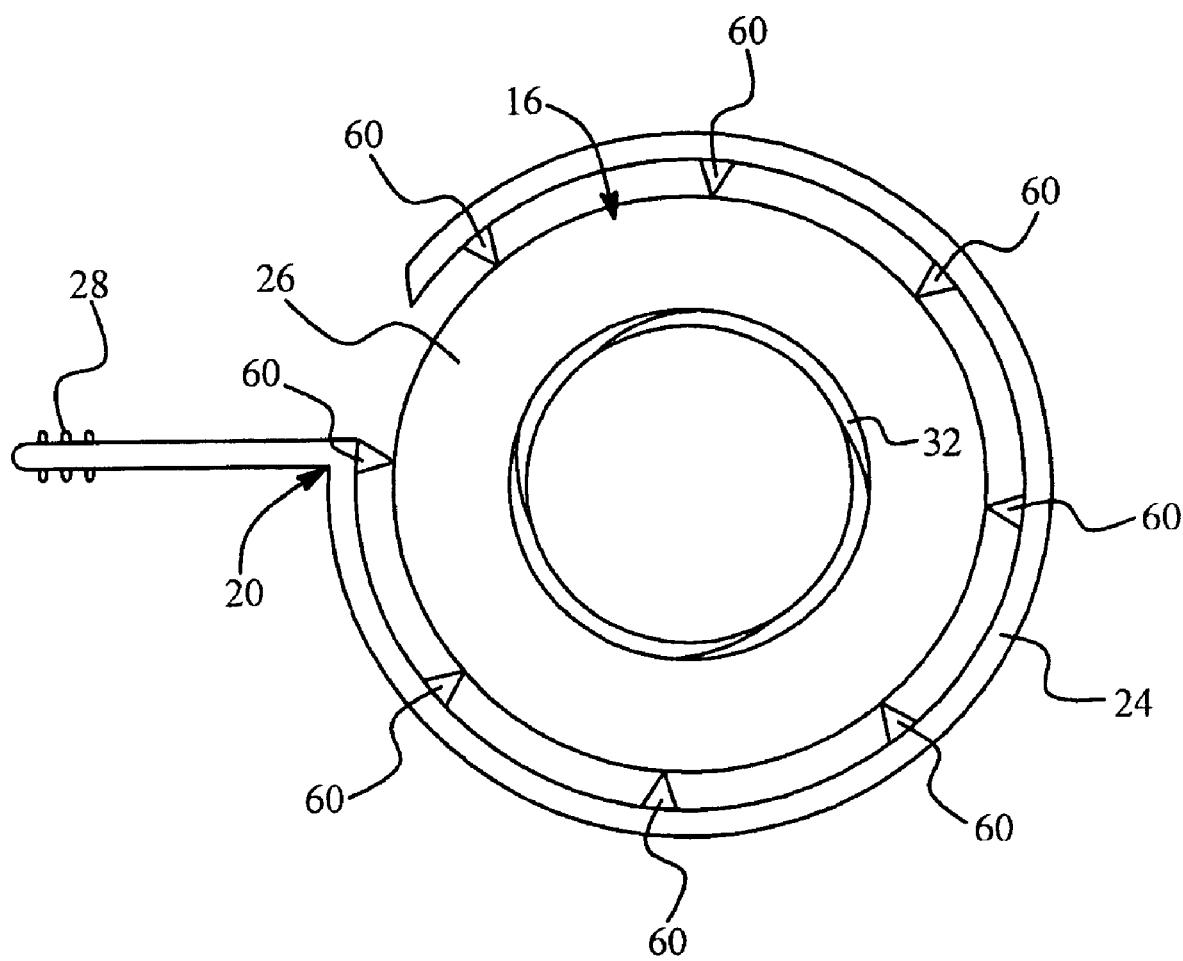
FIG. 11 is a plan view showing multiple frangible fixtures of the safety tab of the access port of FIGS. 6 to 10.
Figure 12:
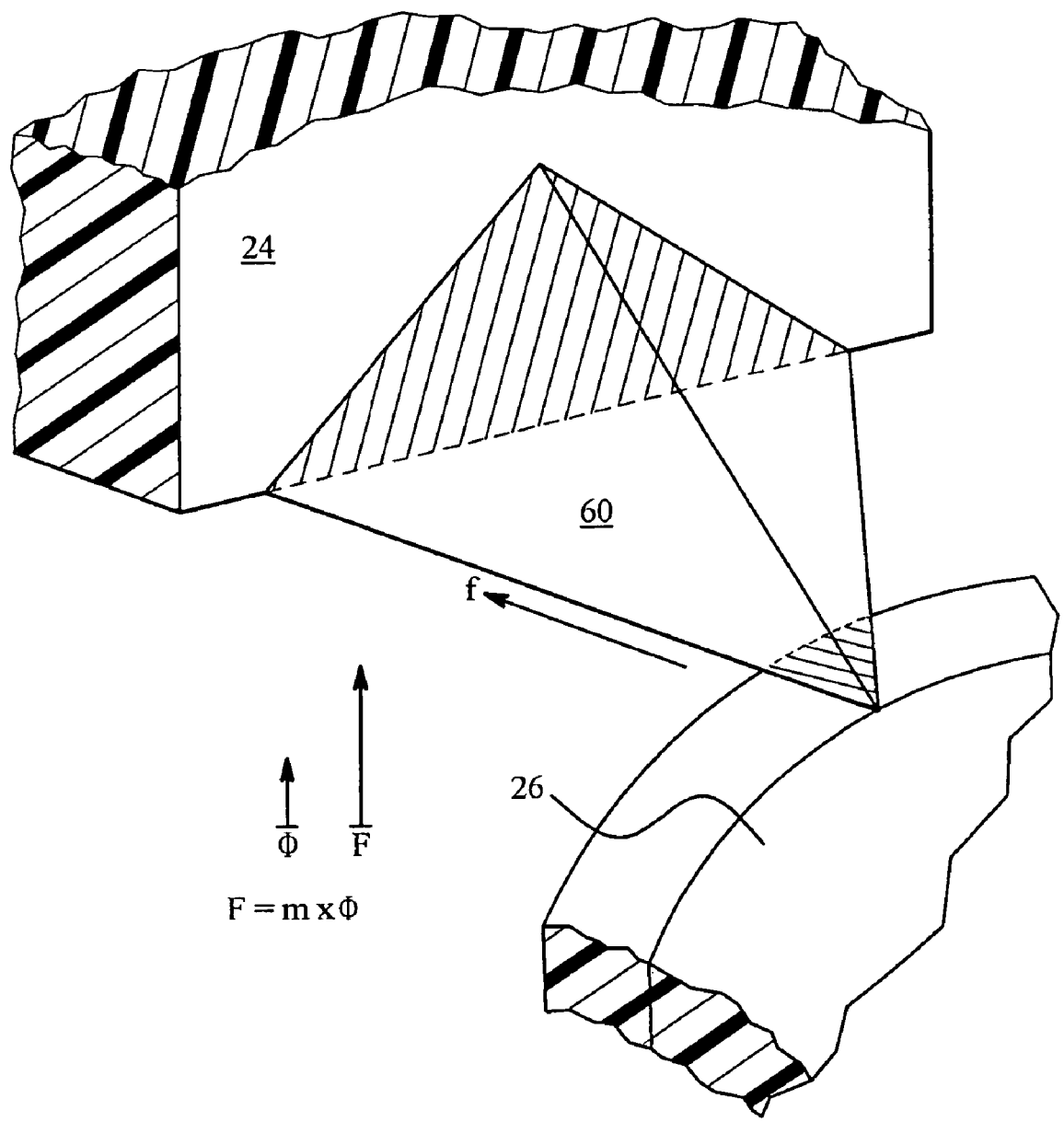
FIG. 12 is a perspective view of one example of the frangible fixtures of FIG. 11.

As seen in FIGS. 11 and 12, ring 24 is connected to flange 26 via a plurality of fixtures 60, e.g., eight fixtures. The number, size and/or shape of fixtures 60 are selected so that the uncoupling of any particular fixture is relatively easy, while the collective tamper resistance force provided by the sum of fixtures 60 is suitably large so that ring 24 of tab 20 does not come free from flange 26 of perforator 16 inadvertently.

In the illustrated embodiment, fixtures 60 are shaped as a tetrahedron, such as a (spherical) tetrahedron (i.e., some faces of the polyhedron are curved). In the illustrated embodiment, one of the faces of each fixture 60 is integral with or attached to ring 24, while a substantially point-type contact is made with the opposing tip of the fixture 60 and flange 26 of perforator 16. In this manner, fixtures 60 come free with ring 24 of tab 20, leaving the edge of flange 26 at least relatively clean so that flange 26 of perforator 16 can move smoothly through shell. It should be appreciated however that shell 12, ring 24 and flange 26 could be sized such that one of the faces of each fixture 60 is integral with or attached to flange 26, while a substantially point-type contact is made with the opposing tip of the fixture 60 and ring 24 of tab 20.

As seen in FIG. 12, the geometry and orientation of each fixture 60 offers the weakest tamper or tear resistance in a direction at least substantially parallel to the plane of flange 26 of perforator 16 (in a direction at least substantially perpendicular with stem 36 of perforator 16 and shown by force arrows f, $\phi$ and F). For example, assuming eight fixtures 60 are made out of polypropylene, a contact with a curved triangular contact zone of 0.6 mm high and 0.3 mm wide between the fixture 60 and the ring 24, can yield a collective tamper resistance force F (eight times the individual tamper resistance force $\phi$) of about forty to eighty Newtons, but each individual tear resistance force f is about five to ten Newtons with a curved triangular contact zone of 0.3 mm high by 0.5 mm wide between the fixture 60 and the flange 26. Using the above-described configuration, tear resistance force f and tamper resistance force F can be optimized.

The operator connects a device such as an administration set with luer connector to the perforator 16 in a fluid-tight manner by removing cap 18 and connecting the device via threads located at the top of the perforator 16. With the perforation assembly 10 installed in the valve 30 and the safety tab 20 removed, arms 22 can be then pressed inwardly to cause perforator 16 to move and puncture the solution container 100b. Fluid flows from container 100b, through stem 36 of perforator 16, through the administration set, and to a patient or other container. In one embodiment, different fluids within container 100b are premixed before the above fluid connection is made.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An access port comprising:
a perforator including an end configured to pierce a medical fluid container, the perforator comprising an end portion configured to connect fluidly to a connector; and
a shell positioned outside of the perforator, the shell including a body and a pair of arms (i) connected hingedly to the body and (ii) extending angularly away from the body toward the piercing end of the perforator, the shell further including members each having a first end connected hingedly to one of the arms and a second end contacting the perforator, the members operable to push the perforator towards a medical fluid container when the arms are pushed towards the body of the shell.

2. The access port of claim 1, which includes a safety tab attached removeably to the shell, the safety tab preventing the perforator from piercing the medical fluid container.

3. The access port of claim 1, wherein the members are each configured to do at least one of: (i) connect to a middle part of one of the arms and (ii) contact a flange extending from the perforator.

4. The access port of claim 1, wherein the perforator and the shell are configured to provide at least one of: (i) audible feedback when the perforator is moved with respect to the shell; (ii) tactile feedback when the perforator is moved with respect to the shell; and (iii) a locked engagement after the perforator has been moved to a piercing position with respect to the shell.

5. The access port of claim 2, wherein the safety tab includes a ring that initially prevents the perforator from piercing the medical fluid container.

6. The access port of claim 5, wherein the ring connects to the perforator via a plurality of frangible fixtures.

7. The access port of claim 5, which includes a flange extending from the perforator, the ring connected to the flange via a plurality of frangible fixtures.

8. The access port of claim 5, wherein the safety tab includes a handle connected to the ring, the handle configured to be manually grasped and pulled.

* * * * *